US008016416B1

(12) United States Patent
Straus

(10) Patent No.: US 8,016,416 B1
(45) Date of Patent: Sep. 13, 2011

(54) AUTOMATIC SYSTEM AND METHODS FOR MEASURING AND EVALUATING AT LEAST ONE OF MASS VISION, COGNITION, KNOWLEDGE, OPERATION SKILLS, AND THE LIKE

(75) Inventor: Sandy Helene Straus, Tucson, AZ (US)

(73) Assignee: Sandy Helene Straus, Tucson, AZ (US)

( * ) Notice: Subject to any disclaimer, the term of this patent is extended or adjusted under 35 U.S.C. 154(b) by 825 days.

(21) Appl. No.: 11/333,953

(22) Filed: Jan. 17, 2006

Related U.S. Application Data

(60) Provisional application No. 60/644,499, filed on Jan. 15, 2005.

(51) Int. Cl.
*A61B 3/00* (2006.01)
*A61B 3/02* (2006.01)
*G02F 1/1335* (2006.01)

(52) U.S. Cl. .................... 351/200; 351/222; 349/12

(58) Field of Classification Search .................. 351/200, 351/222–223, 237, 239, 240–244; 349/12, 349/16
See application file for complete search history.

(56) References Cited

U.S. PATENT DOCUMENTS

| 5,888,074 | A * | 3/1999 | Staplin et al. ................. 434/258 |
| 6,350,032 | B1 * | 2/2002 | Menozzi et al. ............... 351/239 |
| 2003/0223038 | A1 * | 12/2003 | Alster et al. ................... 351/211 |
| 2005/0225720 | A1 * | 10/2005 | Ridings .......................... 351/200 |

OTHER PUBLICATIONS

SpecialtyAutomated Green Catalog, 2008, Boca Raton, Florida Online only: http://www.specialtyautomated.com/catalog.pdf.

Straus, Sandy Helene. 2007. Online Cognitive Tests are Now Needed to Assess the Risk of the Driver With Dementia, Canadian Medical Association Journal, Electronic Letter, Dec. 20, 2007.
Straus, Sandy Helene. Standardization and Computerization of the Clock Drawing Test; Assistive Technology Research Series, vol. 20, 2007, Challenges for Assistive Technology—AAATG 2007, Edited by Gorka Enzymental, J. Aikoitia, G. Cradpock, ISBN 978-1-58063-791-8, pp. 248-253.
Straus, Sandy Helene. New Online Tool Detects Brain Impairment Cuts Older Driver Draths, Online, in Senior Driving Issues, Elder Law e-News, American Bar Assoc. 2007.
Straus, Sandy Helene. Use of the Automatic Clock Drawing Test to Rapidly Screen for Cognitive Impairment in Older Adults, Drivers, and the Physically Challenged, Journal of the American Generatics Society, vol. 55, issue 2, 310,311.
Straus, Sandy Helene. Senior Driver Program Unfair; San Luis OB15PO Tribune, Jan. 31, 2007.

(Continued)

*Primary Examiner* — Scott J Sugarman
*Assistant Examiner* — Dawayne A Pinkney

(57) ABSTRACT

Integrating automatic systems and methods for rapid and objective mass tests, evaluations, measurements, screenings, trainings, or any combination thereof are realized. In a preferred embodiment, a multifunctional system, constructed in the form of preferably a unitary housing, contains automatic methods such as those for evaluation and measurement of at least one of cognition, operation skills, vision, or the like. Authentication identification data of examinees may be processed according to at least one device-dependent process, which may be specific to particular manufacturers, device classes, or other partitioning schemes. The data may be iced, stored in a repository, and utilized for at least one of clinical, educational, medical, military, security, or transport purposes, such as controlling the issuance, restriction, or confiscation of one's license, or ability to operate a vehicle in motion. Automatic systems and methods are paramount to promoting safety and uniformity of testing.

10 Claims, 9 Drawing Sheets

OTHER PUBLICATIONS

Straus, S. 2006. Improving Medical Care and Knowledge of Through New and Rapid Automated Cognitive Impairment Screening Tools, Annals of Family Medicine, Electronic Letter, Dec. 2006.

Straus, Sandy Helene, "New Improved Comprehensive and Automated Driver's License Test and Vision Screening System," Department of Transportation and Federal Highway Administration, FHWA-AZ-04-559(1) Online Research Paper & Online Report Note, 2005.

Straus, Sandy Helene, "A Call for Transportation License Reforms," Presented to the United States Department of Transportation, Washington, DC. 2005.

* cited by examiner

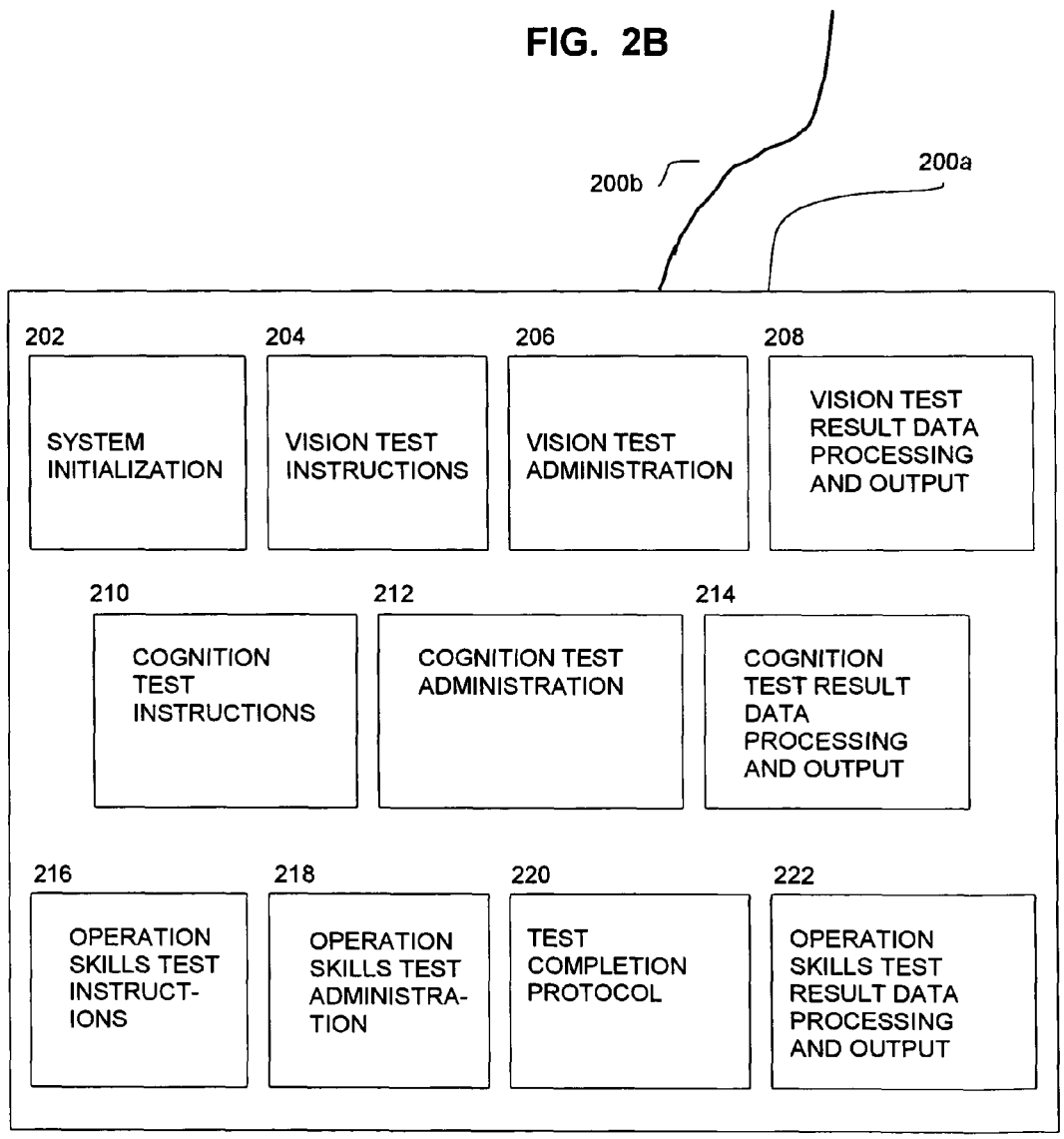

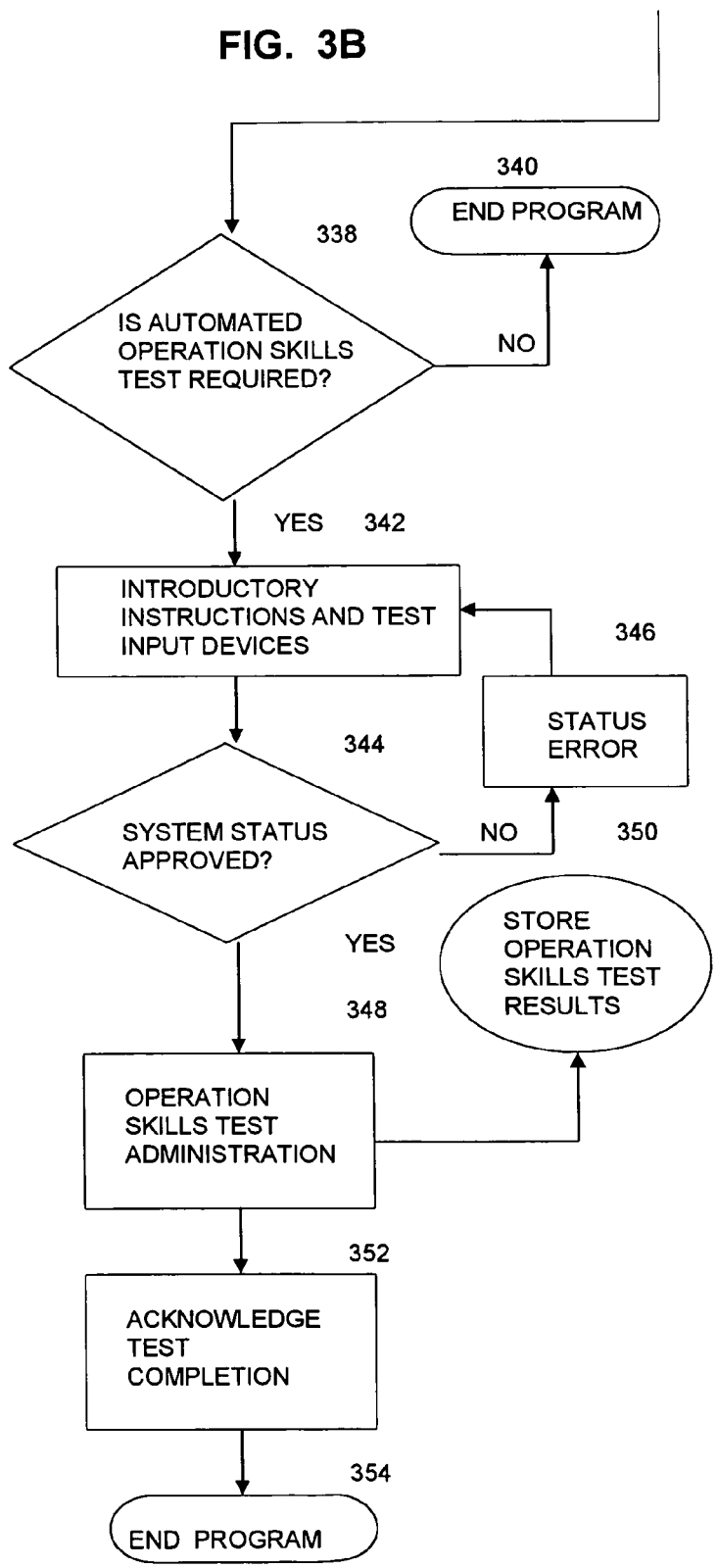

AUTOMATIC SYSTEM AND METHODS FOR MEASURING AND EVALUATING AT LEAST ONE OF MASS VISION, COGNITION, KNOWLEDGE, OPERATION SKILLS, AND THE LIKE

CROSS REFERENCE TO RELATED APPLICATIONS

This application claims the benefit of provisional patent application Ser. No 60/644,499, filed 2005 Jan. 15 by the present inventor.

FEDERALLY SPONSORED RESEARCH

Not Applicable

SEQUENCE LISTING OR PROGRAM

Not Applicable

BACKGROUND—FIELD

BACKGROUND—PRIOR ART

Non-automatic tests tend to be subjective, time-consuming, costly, and heavily reliant on the experience of the examiner. Such tests also tend to significantly contribute to electronic waste (e-waste), paper waste, and deforestation, three serious threats to our planet and environments.

Non-automatic systems and methods suffer from a variety of problems. They are inadequate forms of measuring visual, cognitive, and related capabilities. No empirical evidence appears to support the effectiveness of current methods, such as those designed to screen individuals for licenses to operate vehicles in motion. A vehicle in motion includes but is not limited to an aircraft (any vehicle capable of flight), automobile, military vehicle, motorcycle, spacecraft (any vehicle that travels in space), tractor (any vehicle used in agriculture applications), train, truck, watercraft (any vehicle that travels in or on water), or the like. A lack of automated and comprehensive test measures may account for this dearth of data. Still further current non-automated methods also fail to adequately, fairly, and rapidly screen inmates and law enforcement personnel in security agencies, students in educational institutes, patients in medical establishments, and service personnel and veterans of militaries, among others. Non-automatic testing techniques are also associated with mechanical failures, long queues, cheating, memorization of testing materials, and costliness. Extra time and paperwork are required for scoring and recording purposes. Still further, a lack of non-automatic instruction and scoring introduce bias into the testing processes.

Non-automatic testing also lacks the capability to dynamically simulate conditions that exist, especially, for example, when one operates a vehicle in motion. Such non-automatic techniques also complicate the process of testing and evaluating the masses of individuals who, for example, seek licensure to operate a vehicle in motion or require annual or periodic health examinations. Non-automatic vision screening machines, for example, are severely limited by their static conditions and inability to screen individuals for both potential eye diseases and vision loss conditions. Studies show that these devices also tend to contribute to test fraud and memorization of optotypes.

Among many advantages, automatic tests ensure equal access and optimization of medicine and medical specialty services to all patients, regardless of age, culture, disability, education, ethnicity, gender, language, race, or socioeconomic status. Automatic tests also contribute to equality in education, including training and teaching practices. Automatic tests reduce, if not eliminate, fraud. Automatic tests standardize administration, scoring, interpreting, and reporting of test results with automatic feedback. Therefore, one of several embodiments of my automatic systems and methods compensates for impediments associated with non-automatic measurements and evaluations of vision, cognition, operation skills, or the like of individuals.

No automatic systems and methods, such as those presented herein, are available-today that adequately, economically, thoroughly, and uniformly measure in whole or in part, an individual's vision, cognition, operation skills and related capabilities. There exists a major need for systems and methods that automatically provide measures for at least one of licensing Erne to operate a vehicle in motion, returning to military duty, improving security, promoting safety, monitoring health, ensuring equality in education, or screening those who are incarcerated. In militaries, there remains a great demand to rapidly and uniformly screen recruits, soldiers, and veterans for cognitive deficits, vision impairments, among others for recruitment, fitness for duty, and return to duty measures.

Today's license testing practices and equipment for operating vehicles in motion are antiquated and inadequate. For example, the current testing standards for driver's licenses, which tend to influence other sectors of transportation and impact driving standards in other countries, remain unchanged for more than seven decades. Each year, there are millions of collisions and injuries on American roads. Thousands of motorists are killed. Drivers with at least one of vision impairments, cognitive decrements, or the like may not know that they pose a risk to themselves and other motorists. Yet no driver's license bureau offers automatic vision, cognition, and driving skills testing programs.

It is important to note that cataracts, Age-related Macular Degeneration (AMD), glaucoma, and diabetic retinopathy account for the four main causes of visual impairment and blindness in the United States yet these are not currently screened in any transportation agency for licensure purposes. Some diseases, such as glaucoma, are insidious. All are expected to jump in the next fifteen years. Still further, non-automatic and static visual acuity devices and eye charts are used to measure visual abilities of drivers, pilots, and others. Yet, dynamic visual acuity, a measurement of the ability to discern detail of objects in motion, is not automatically offered for any transport or medical application.

Cognitive and psychomotor abilities mediate and influence the actions of individuals. The capacity to understand and effectively interact with the environment is crucial for operating a vehicle in motion. Advancing age, disease, and trauma reduce cognitive, motor, sensory, and visual abilities, and impact psychomotor performance. Head trauma and eye trauma, common among victims of war, collisions in vehicles of motion, and falls are particularly damaging yet these are not easily detected or monitored with prior art devices. Yet, until now, no automatic tests exist that can rapidly, uniformly, and effectively detect cognitive impairments, such as Traumatic Brain Injury, a leading cause of death and disability in motor vehicle accidents and wars.

Dementia, although primarily associated with older people, occurs in people of all ages, particularly the middle-aged. It sometimes proves hazardous to drivers who may lose their sense of time or direction. While there are various stages and varieties of dementia, it is necessary to screen individuals because conventional testing methods and self assessments may not easily detect this condition. Also, a person with dementia may not recall any self-assessments. A driver with dementia poses risks to motorists. In the USA, as well as many other countries, no federal or state laws specifically mandate cognitive screening tests for drivers. Yet driver's license test personnel are not medically qualified to determine whether or not a driver has dementia or any cognitive impairment. Still further, only skilled or trained clinicians are qualified to administer and score tests, yet a lack of uniformity and automation prevents widespread use of cognitive tests. For these reasons, automatic, user-friendly, and interactive cognitive tests are needed to provide rapid and useful measures of cognitive performance.

Since studies show that the incidence of dementia is expected to jump 400% over the next twenty years, it is a public health priority to implement cognitive tests, in particular, automatic cognitive tests that may be used to detect, monitor, and treat dementia. The use of automatic tests is now also needed to at least identify, observe, or monitor dementia in drivers and others who operate vehicles in motion, to recommend medical follow-ups, and to improve road safety.

Furthermore, simulation devices, commonly known as simulators, may prove to be useful for transportation license screening purposes. Simulators simulate, reproduce, and/or represent under test conditions phenomena likely to occur in actual performance. Simulators are also used to teach or assess transportation skills, among others. Some simulators are actually deployed and utilized as trainers, especially in military applications. Simulators also afford the ability to screen driving abilities, with little or no risk of injury, and to offer tests associated with at least one of vision, cognition, or operation skills. An example of a simulator is a driving simulator, generally used to teach or assess driving skills. Driving simulators, as an example, offer the advantages of ambient light, weather, pavement, signage, and driving conditions, such as traffic and pedestrian movement, among others, that are almost simultaneously or consecutively impossible to encounter during an actual on-road driving test. Currently, no driving simulators exist in any driver's license bureau or other transportation license agency in the United States. This stems primarily from high costs and simulator sickness concerns that some perceive as impediments to driving simulators.

Driving simulators also provide an alternative to driver's license test staff members who may have concerns about their safety and the safety of the examinee when conducting on-road driving tests with examinees of unknown skill or experience. As gas prices increase and driver's license bureaus are burdened with staffing matters and motor vehicle maintenance costs, simulation may prove to be a cost-effective, quick, and eco-friendly method of conducting and/or supplementing traditional on-road driver's license tests, with little or no staff intervention.

Simulators, such as driving simulators, are generally available in the 1-screen cab, 3-screen cab, 1-screen desktop, or 3-screen desktop, dome, and projection room models. Simulators, also referred to as trainers, are designed to optimize realism and overall training assessments in various settings. Simulators vary in cost, space considerations, and options. For example, the 3-screen models tend to require additional expense and space. Although they may also account for a greater susceptibility to simulator sickness and possible aftereffects, they also provide a more realistic view of driving. Other simulators and trainers are commonly used to educate pilots, soldiers, conductors, captains, astronauts, military tank drivers, security officers, and commercial drivers, among others. These simulators may include but not be limited to flight simulators, train simulators, ship simulators, space flight simulators, military simulators, bus simulators, and truck simulators.

Therefore, the use of simulators is not intended to be limited to automobiles. For example, control devices may be devices commonly found on all vehicles in motion, including but not limited to airplanes, boats, military tanks, spaceships, steamships, tractors, trains, and the like. For example, an examinee in need of an operations test for a maritime license would be positioned before a driving simulator with at least one of maritime features or applications. The tests would be programmed accordingly as one skilled in the art would know.

Although computerized knowledge tests are offered in some driver's license bureaus, there is uncertainty as to their effectiveness. A lack of automation and a lack of standardization of these tests pose challenges to safe driving. For example, in the United States, the laws or signs governing a road in a mountainous state may not apply to those in a non-mountainous state. Yet, the drivers from a non-mountainous state, who may lack the skill to drive on mountainous terrain, may drive in a mountainous state and vice versa.

Nowhere is the need for improved testing more obvious than in healthcare, military, security, and at the driver's license bureaus, among other transport agencies. In the healthcare industry, automatic testing methods are needed due to challenges associated with medical care access, time constraints, language barriers between clinicians and patients, emergency service responses, staff shortages, and the effective delivery of medical consultation and treatment to the masses. Yet, studies show that nearly 20% of Americans lack basic health care coverage. Consequently, millions of drivers may not have access to regular or periodic vision examinations, cognitive tests, and related evaluations in a medical setting. These drivers may constitute a serious collision risk because they may not be aware that their vision, cognition, and/or operation skills may be declining or posing threats to themselves and to others.

Since it is illegal to operate a motor vehicle without a driver's license and driver's insurance in the United States, the onus then falls onto the state driver's license bureaus to adequately screen all drivers, including the uninsured, for visual, cognitive, and related impairments. Yet, as discussed earlier, the driver's license test department personnel are not medically qualified to determine whether or not a driver has a cognitive, visual, or other impairment. Therefore, these personnel cannot decide who can or cannot drive. Long lines and staff shortages are commonplace at driver's license test offices. Many offices now face closure. Meanwhile, millions of hours of labor, gallons of gasoline, and dollars in equipment are annually wasted. Collectively, this leads to an excessive amount of pollution that can be significantly reduced by automatic systems and methods of testing individuals.

The disproportionate number of automobile collisions, fatalities, and deaths also underscores the needs for improved testing technologies and methodologies. The devices and systems currently in use fall short of attempting to arrest the effects of aging, disease, disorder, injury, and trauma of the eyes and brain, among others.

Rather than focus on possible underlying causes of these collisions, such as driver's license testing methods, many people and organizations unjustly seek to solely accelerate the frequency of license renewal and testing periods. While these on-site driver's license tests may, in the short term, allow for limited identification of drivers with impairments, they completely fail, in the long term, to improve the actual screening process and identify the most at-risk drivers. Still other organizations promote participation in short-term driving skills assessments, courses, or seminars or the use of self-testing tools. While helpful, the law does not mandate these options. There exists no scientific evidence that demonstrates that many drivers are active participants in these activities and that the individuals who utilize these assessment courses or tools volunteer to cease operating a motor vehicle on the bases of their scores. Many individuals, particularly at-risk drivers, may not want to surrender their driver's license if they do not have alternative means of transportation. Hence the acceleration of license renewal frequencies and testing periods, the short-term driving skills assessment courses, and the self-testing tools only create a placebo effect because it is the actual driver's license testing methodology that requires automation and improvements as my automatic systems and methods provide. Once testing enhancements are in place, the accelerated driver's license renewal periods and short-term driving skill assessment courses serve as supplementary and precautionary safety measures.

As populations significantly increase, the demand for more effective license screening tools intensifies. These are issues that most states and countries now face as the older adult population grows and necessitates adequate accommodations and testing methods to improve the safe operation of vehicles in motion. Although widespread among motor vehicle drivers, similar challenges exist among applicants and licensees in air, marine, rail, space, and military settings as individuals live longer and work longer.

Moreover, national and international security concerns persist. Proposals and laws calling for a national driver's license, for example, may not be viable if an automated driver's license test is not implemented to reduce long lines, promote the sharing of data between states, and positively identify drivers. Additionally, the absence of standardizations of screening test methods, scoring, and/or reporting invites a number of individuals who may not qualify for a license in one state to obtain a license in another state. Fraudulent schemes and issuances of driver's licenses, commercial driver's licenses, pilot's licenses, and hazardous materials transportation licenses pose threats to national and international security.

Automation and comprehensive testing methodologies are now needed to standardize competency testing of individuals. In militaries, there exists a great demand to rapidly and uniformly screen recruits, soldiers, and veterans for recruitment, fitness for duty, and return to duty measures. Still further, in the security fields, automatic testing methods are sorely needed for objectivity. Automation and comprehensive testing methodologies are also used to improve exchange of data between agencies that need it the most. For example, an examinee who fails a vision test for a driver's license should be prohibited from obtaining a pilot's license. Yet, if both the driver's license bureau and the aviation agency offer automated testing and sharing of data, then this examinee is not issued a license at either agency.

Equipment, procedures, and policies to obtain or maintain licenses to operate vehicles in motion, for example, vary from state to state, country to country, and agency to agency. In some aviation, maritime, and rail agencies, requirements are limited to a physician's evaluation. However, not all physicians are trained to detect visual, cognitive, operation skills, and related decrements. At driver's license bureaus, testing is generally limited to a static visual acuity test, a road test, and a written test. The written test usually covers accident prevention, pavement marking identification, safety rules, signal identification, traffic laws, traffic signage identification, and vehicle equipment. Dynamic visual acuity tests, among others, are needed to provide the genuine experiences and challenges of discerning details of objects in motion that every driver encounters in every sector of transport.

Hence the mass screening tests previously developed lack the unification or parsimony of methods outlined herein.

The prior art discloses different vision tests and screening methods. These non-automated visual acuity tests typically define an individual's ability to read known letters or numbers of different sizes at various distances. For example, the Snellen Eye Chart, developed in 1862 by Dr. Hermann Snellen, a Dutch ophthalmologist, is generally prescribed under ideal conditions (daytime lighting) and the absence of extraneous light sources. Yet, visual acuity does not provide a comprehensive vision assessment. Eye charts are particularly ineffective because patients can see dark letters through the cataract. Patients may also easily memorize rows of various Snellen acuity charts. Fink and Sudan (2004) show that Snellen acuity, the most widely used vision testing measure, accounts for less than 0.1 percent of the visual field and fails to quantify contrast sensitivity and color vision, two of several visual parameters needed for operating a vehicle in motion. Vision screen tests therefore require contrast sensitivity measurements because visual acuity may appear normal yet the ability to perceive patterns may diminish.

Prior art non-automated screening devices have the disadvantage of test administration complexities, machinery breakdowns, cheating, and increases in the probability of incurring an error with respect to determination of results, such as scoring.

Other known tests involve situational awareness, which does not include a test for vision condition. Situational awareness tests are targeted particularly towards the automobile driver and are not suitable for other vehicles in motion.

Computer-based visual field tests have been employed to test for visual diseases, such as glaucoma and age-related macular degeneration (AMD). For example, the prior art discloses the use of three-dimensional Amsler grid tests, such as disclosed in U.S. Pat. No. 6,578,966 to Fink et al. and U.S. Pat. No. 6,769,770 to Fink et al.

Although these patents are generally satisfactory for their intended purposes, they are not completely automated because they require assistance or interpretation of complex output following the screening process. They do not include a mechanism for preventing cheating or dishonorable test taking practices. These tests can now be mastered when both eyes, rather than one eye, are wide open. Such technicalities limit the ability to adequately and effectively evaluate each eye independently for disease. The test also needs to efficiently evaluate each eye at a faster pace than the current time now. Other methods, in addition to Fink et al., do not provide user authentication identification techniques and automatic instruction to initiate the test process.

These and other limitations of the prior art are overcome by my automatic systems and methods.

An interactive method is disclosed to effectively and economically screen individuals by, among other things, rapidly affording them vision, cognition, and related screening examinations.

Automatic testing is fast, simple, objective, and cost-effective. It provides comprehensive screening unlike any available. It also offers such features as those to reduce labor, cheating, memorization, and transcription errors.

Another benefit of this improved testing system would be the reduction of collisions, particularly on the roadways, due to increased numbers of examinees and frequencies of tests, and likely, in all sectors of transportation.

Many accidents can be avoided if individuals are adequately screened for visual, cognitive, and related decrements, such as operation skills. Clearly, a system that could screen many people could spare many lives and serious injuries, as well as reduce related property damage and the likelihood of collisions.

The automation and exchange of data and information between transportation agencies may ultimately result in significant cost-savings, especially through the avoidance of repeatability of certain vision, cognition, and related tests. Such assessments allow for extensive transportation applications.

A greater number of older adults are licensed to operate vehicles in motion now more than ever before. Based on these trends, a surge in the number of licensed older adults are expected. These changes may also include a significant rise in the number of collisions, injuries, and fatalities among older adults unless action is taken now to screen and ultimately monitor incompetent drivers, novice drivers, and at-risk drivers of all age groups.

Schools may also benefit from the cost-effective and comprehensive mass screening of numerous students that some embodiments of my automatic systems and methods afford.

Automatic systems and methods may also be used to identify individuals, irrespective of their residency. Such approaches to identification would simplify licensure processes and ultimately reduce security threats, pollution, paperwork, and bureaucracy.

Automatic systems and methods can also improve local, national, and international security as these relate to driver's licenses and other documents introduced through The 9/11 Commission Report (2004) (by The 9/11 Commission Report Implementation Act of 2004, S.2774) and The Intelligence Reform Bill. The Intelligence Reform Bill, signed into law by President Bush, Dec. 17, 2004, requires federal agencies to implement uniform driver's license issuance standards for the U.S. States. H.R. 418 (Feb. 8, 2005) allows for the bill ". . . to establish and rapidly implement regulations for State driver's license and identification document security standards . . . "

Improved automatic systems and methods of measurements and evaluations are also useful for individuals with special needs or various disabilities. Such systems and methods empower such individuals and level the playing field in a computing environment. Such "one size fits all" approaches to testing may significantly reduce the need for special accommodations such as sign linguists, specially equipped motorized vehicles, etc. For the hearing impaired, for example, the testing instructions can be provided both visually and audibly on the screens. For those who are unable to write or hold a writing instrument, such as those with movement or neuromuscular disorders, they may actively and independently engage in testing processes. Studies show that improved automatic systems and methods allow for individuals with such physical inabilities to fully participate in cognitive tests that were, until now, limited to individuals without such disabilities.

Therefore, strong needs exist for systems and methods that provide automatic, comprehensive, quick, objective, economical, and user-friendly measurements and evaluations of vision, cognition, operation skills, and the like of the masses. Still further, solutions that cause little or no harm to environments and planet are now needed to reduce the massive amounts of e-waste, deforestation, and pollution each year. Improved automatic systems and methods meet such needs.

Thus several advantages of one or more aspects are to automatically provide rapid, objective, and effective testing of the masses for at least one of vision, cognition, operation skills, or the like. Other advantages of one or more aspects are to improve national and international safety and security through authentication identification data of examinees and test fraud prevention mechanisms. Other advantages of one or more aspects are to improve safety in the roads, rails, skies, waters, and space. Still other advantages of one or more aspects are to conserve energy, prevent deforestation, and reduce pollution associated with paper, computers, software, and e-wastes. These and other advantages of one or more aspects will become apparent from consideration of the ensuing description and accompanying drawings.

SUMMARY

In view of the disadvantages and shortcomings present in the prior art, multifunctional automatic systems, constructed in the form of preferably a unitary housing, comprise methods such as those for mass evaluation and measurement of at least one of vision, cognition, operation skills, or the like.

DRAWINGS—FIGURES

In the drawings, closely related figures have the same number but different alphabetic suffixes.

FIG. 1A illustrates a depiction of an embodiment of automatic systems and methods of measuring and evaluating at least one of vision, cognition, operation skills, or the like;

FIG. 2B illustrates an embodiment of a block diagram of operational components;

FIGS. 3A-3B show an embodiment of a flowchart of automatic systems and methods;

DETAILED DESCRIPTION OF PREFERRED EMBODIMENTS

Embodiments of the automatic systems and methods that measure and evaluate at least one of vision, cognition, operation skills, or the like are presented herein.

It will be appreciated that the preferred embodiments may be readily implemented in any form that executes automation. This includes software that may be used on a variety of hardware platforms. Alternatively, the disclosed system may be implemented partially or fully in hardware using standard logic circuits. Whether hardware, software, or any other form that executes automation is used to implement the system varies depending on the speed and efficiency requirements of the system, the particular function of such systems, and the particular systems, such as microprocessor or microcomputer systems.

In the first illustration, for example, we may assume that the unitary housing encompasses comprehensive screening including all elements of a vision test, cognition test, and operation skills test. However, a client may only require one kind of screening, such as a vision test. In this case, there may only then be a requirement for system initialization, vision test instructions, vision test administration, vision test completion protocol, and vision test result data processing and output. Although a preferred embodiment is shown for use with one system, it should be clearly understood, that use with other computerized systems, methods, devices, and/or simulators, are integrable. Systems and/or related devices may be connected locally, remotely, wirelessly, through a thin client, and/or any other means for data exchange, transmission, and sharing. Thin clients, for example, save space and may be ergonomically and economically feasible for places such as transportation bureaus, homes, medical facilities, security agencies, militaries, or the like. Since a thin client performs most of its processing on a central server or at some centralized managed site, very little hardware and software are usually required at the examinee's location.

When there are no disorders detected through any automatic tests, the examinee may be notified through automatic output or passing scores on tests completed.

Figure 1A:
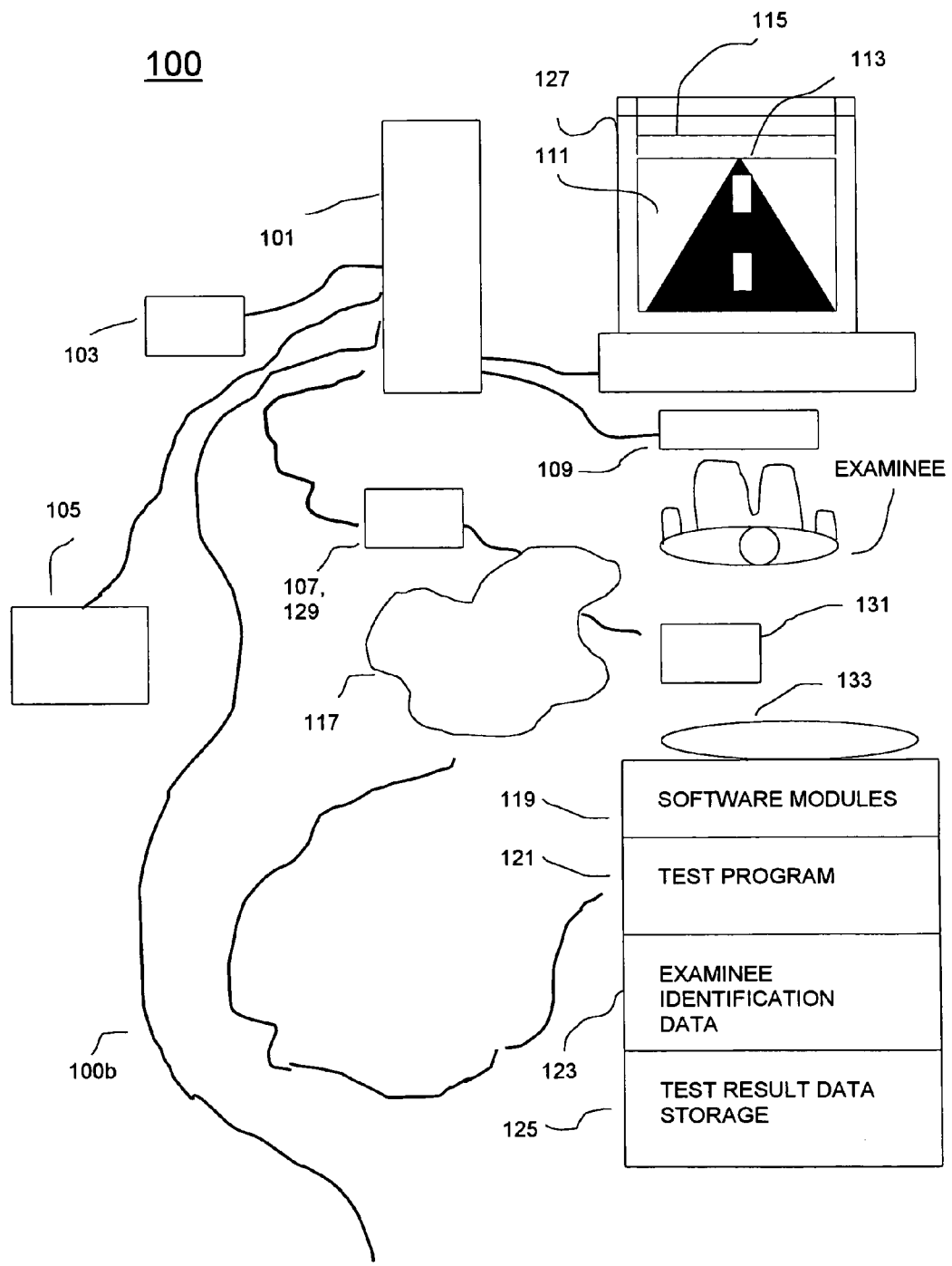

Turning now to the drawings, FIG. 1A illustrates, in schematic block diagram, an example of the system 100, including any interconnected network for data transmission, sharing, and exchange, 117, such as an Internet, Intranet, Extranet, or the like, independent of location. Instruction data is displayed. The examinee is positioned at a predetermined distance in front of a display device, such as monitor 127. In this embodiment, there is one display device, such as a monitor. However, in order to provide a more realistic view of features such as those inherent to certain tests (for example, a road for a driving test), among others, for such tests as operation skills, vision, or certain cognition tests, more than one display device, may be incorporated. To authenticate, establish, update, or modify the identification of the examinee, which is generally necessary when screening tests of the masses are performed, a user identification input device, 103, based on information data input, such as biometrics, thermal imaging, radio frequency identification (RFID tags), or the like can be used. Such information can be stored or retrieved through the examinee identification data 123. Examinees connect to the system 100 through the use of a communications device or connection device such as a modem 107 or a connection device, such as a computer network interface card 129 installed in a device that accepts information in digital or similar form and manipulates it for a result based on a sequence of instructions, such as a computer 101 or the like. A displaying device, such as a computer program used for accessing sites or information on a network, or standard browser 115, such as Netscape Navigator®, Firefox®, Google Chrome®, Apple Safari®, or Microsoft Internet Explorer®, can be used to remotely access a group of electronic pages generally connected to one another, such as a website 131 established by a device that provides information and services, such as server(s) 133. However, the system can consist of any integrable displaying device. Website 131 preferably includes the use of text, digital images, audio and/or video, developed using conventional software tools and languages, such as ActiveX technology, C++, Java, and/or HTML, among others.

The examinee can respond to observed test stimuli. The system comprises user input device(s), 109, such as at least one of the following, computer mouse, wireless mouse and pad, keyboard, touch screen, joystick, brake pedal, accelerator pedal, pedal, steering wheel, microphone, camera, horn, virtual reality device, control device fitted with motion sensors, interactive screen, electronic display, or any other device capable of detecting an individual's response to testing stimuli.

Various programmable electronic devices that can store, retrieve, and process data, such as automated and computerized screening tests, can be provided to the examinee using an automated viewer used to access an interconnected network for data sharing and exchange, such as a browser 115, including, for example, unaided cognitive tests, vision tests, and operation skills tests, among others. Such automatic tests can be readily stored on devices that execute automation, such as portable software modules 119, such as Java applets, and then downloaded and executed locally on user's computer 101, or, alternatively, executed on a computer or plurality of computers located at a central facility. Each device that executes automation, such as software module 119 tests for at least one of desired visual, cognitive, operation skills, or related deficiency by displaying to the examinee test stimuli, such as 113, of different color, contrast, frequency, location, shape, size, speed, and/or intensity on a display device, such as monitor 127, and then by recording and comparing what the user reports seeing with what is presented by a device that accepts information in digital or similar form and manipulates it for a result based on a sequence of instructions, such as a computer 101. A calibration program (not shown) may be needed to calibrate display devices, such as monitors of various sizes.

Figure 1B:
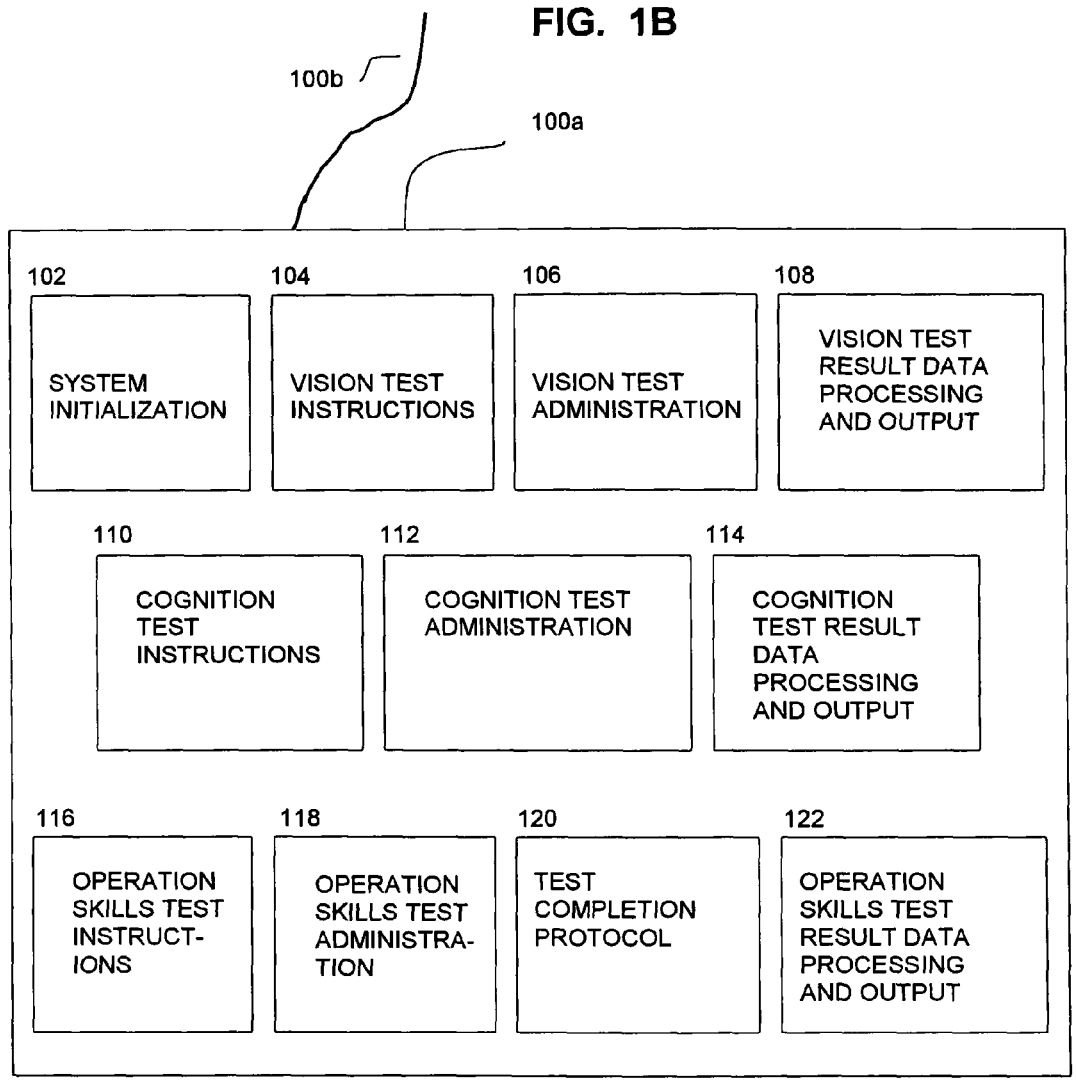
FIG. 1B illustrates an embodiment of a block diagram of operational components.

Server(s) 133 include screening test program(s) 121 incorporated into software module(s) 119. An operating system executes a test program 121 when a test is to be conducted. Test program(s) measure an examinee's visual, cognitive, and/or operation skills capabilities and/or conditions. These tests, as generally defined in 100a of FIG. 1B, include elements of program(s) of the system(s) that implement algorithms for, among other operations, initialization of the system 102, vision test instructions for the test examinee 104, vision test administration 106, vision test result data processing and output 108, cognition test instructions for the test examinee 110, cognition test administration 112, cognition test result data processing and output 114, operation skills test instructions 116, operation skills test administration 118, test completion protocol 120 and operation skills test result data processing and output 122. While connected to computer 101, they may also be directly connected to some remote server. The actual algorithms for each operation, examinee identification, and/or any that may be required for a calibration program (to determine the physical pixel size of display monitor 127 to keep stimuli of the same pixel size the same physical size) being structured in a manner as would be understood by one of skill in the art.

Test stimuli 113 are represented by any of the small discrete elements that together constitute an image, such as pixels, and may be transmitted from a video controller (not shown) within computer 101 or through server(s) 133 to display device, such as monitor 127 having a viewable area 111 representing the surface where the pixels are output. Computer 101 monitors the examinee's response, which is entered by, preferably, the employ of a user input device 109. It also displays test stimuli 113.

Once the examinee's test scores or results are available, these may appear on a display device 127 or through use of an output device, 105, such as a printer, via test result data storage 125. Connection 100b links 100a to a device that accepts information in a digital or similar form and manipulates it for a result based on a sequence of instructions, such as a computer 101.

Figure 2A:
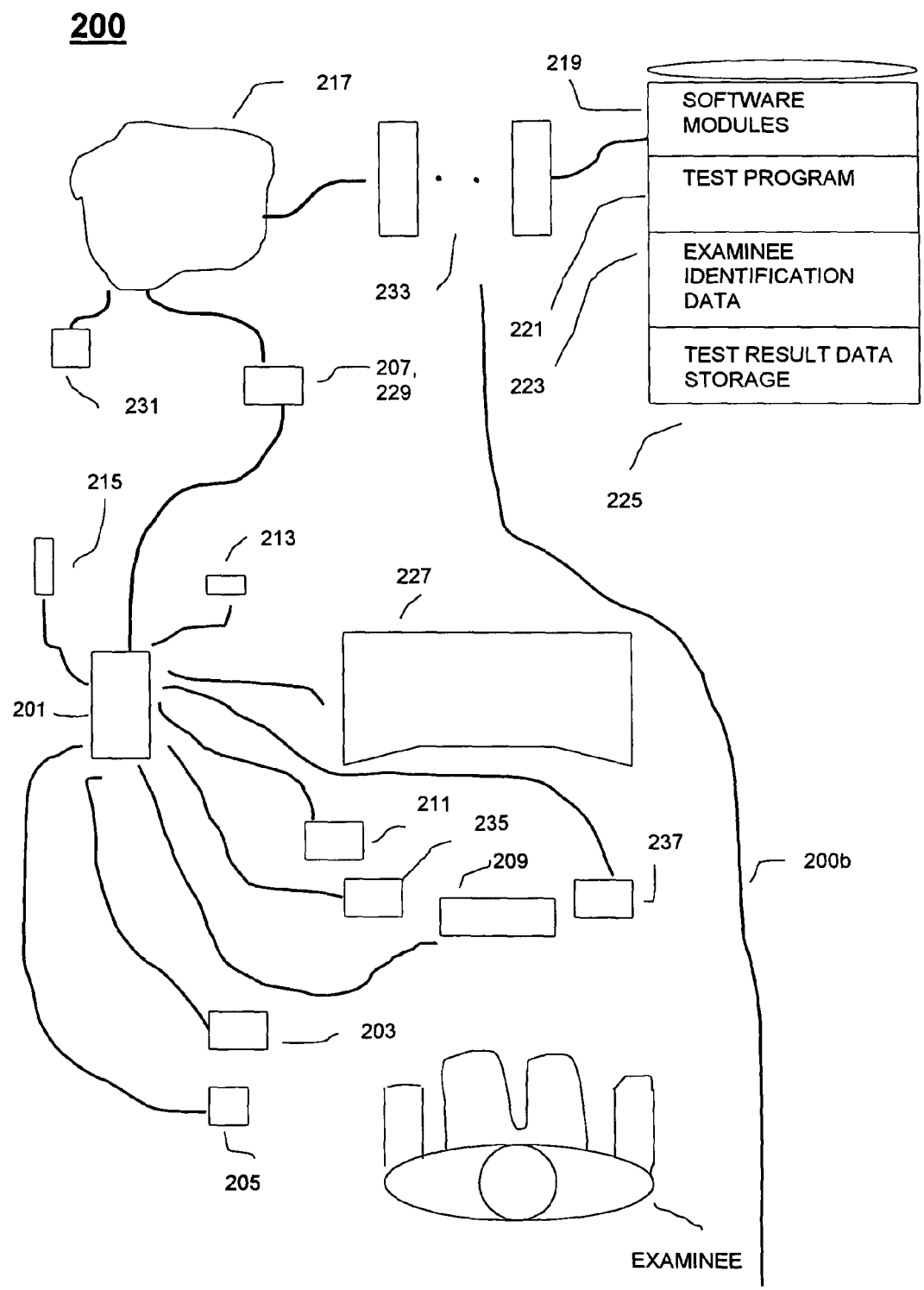
FIG. 2A illustrates another depiction of an embodiment of automatic systems and methods of measuring and evaluating at least one of vision, cognition, operation skills.

FIG. 2A depicts a schematic block diagram, at least one example of the system 200, including an interconnected network for data sharing and exchange, 217, such as the Internet, Intranet, or Extranet. An examinee is positioned at a fixed distance in front of a display device, such as a monitor 227. In this embodiment, for example, there are multiple display devices, such as three monitors, which are generally preferred to provide a more realistic view of features such as roads, for such tests as operation skills, vision, or certain cognition tests. However, at least one display device, such as a monitor, may be incorporated. To authenticate, establish, update, or modify the identification of the examinee, which is generally necessary when testing of the masses are performed, a user identification input device, 203, based on information data input, such as biometrics, thermal imaging, radio frequency identification (RFID tags), or the like can be used. Such information can be stored or retrieved through the examinee identification data 223. Examinees connect to the system 200 through the use of a communications device or connection device such as a modem 207 or a connection device, such as a computer network interface card 229 installed in a device that accepts information in digital or similar form and manipulates it for a result based on a sequence of instructions, such as a computer 201 or the like. A displaying device, such as a computer program used for accessing sites or information on a network, or standard browser 215, such as Netscape Navigator®, Firefox®, Google Chrome®, Apple Safari®, or Microsoft Internet Explorer®, can be used to remotely access a group of electronic pages generally connected to one another, such as a website 231 established by a device that provides information and services, such as server(s) 233. However, the system can consist of any integrable displaying device. Website 231 preferably includes the use of text, digital images, audio and/or video, developed using conventional software tools and languages, such as ActiveX technology, C++, Java, and/or HTML, among others. The audio output devices 235 and 237 may constitute a conventional sound card with speakers, all as known in the art.

An examinee can respond to observed test stimuli with the aid of user input device(s), 209, such as at least one of a computer mouse, wireless mouse and pad, keyboard, touch screen, joystick, brake pedal, accelerator pedal, pedal, steering wheel, microphone, camera, virtual reality device, control device fitted with motion sensors, interactive screen, or any other device capable of detecting an individual's response to testing stimuli. In this example, the setup is similar to that of a desktop driving simulator. Therefore, a user input device 211, such as an accelerator and/or brake pedal, can be included.

Various programmable electronic devices that can store, retrieve, and process data, such as automated and computerized screening tests, can be provided to the examinee using an automated viewer used to access an interconnected network for data sharing and exchange, such as browser 215, including, for example, unaided cognitive tests, vision tests, and operation skills tests, among others. Such automatic tests can be readily stored on devices that execute automation, such as portable software modules 219, such as Java applets, and then downloaded and executed locally on user's computer 201, or, alternatively, executed on a computer or plurality of computers located at a central facility. Each device that executes automation, such as software module 219 tests for at least one of a desired visual, cognitive, operation skills, or related deficiency by displaying to the examinee test stimuli, such as 213 of different color, contrast, frequency, location, shape, size, speed, and/or intensity on a display device, such as monitor 227, and then by recording and comparing what the user reports seeing with what is presented by computer 201. A calibration program (not shown) may be needed to calibrate display devices, such as monitors, of different sizes.

Server(s) 233 include screening test program(s) 221 incorporated into software module(s) 219. The operating system executes test program 221 when a test is to be conducted. The screening test program(s) measure the examinee's visual, cognitive, and/or operation skills capabilities and/or conditions. These tests, as generally defined in 200a of FIG. 2B, include the elements of the program of the system that implement algorithms for, among other operations, initialization of the system 202, vision test instructions for the test examinee 204, vision test administration 206, vision test result data processing and output 208, cognition test instructions for the test examinee 210, cognition test administration 212, cognition test result data processing and output 214, operation skills test instructions 116, operation skills test administration 218, test completion protocol 220 and operation skills test result data processing and output 222. While connected to the servers 233, they may also be directly connected to a local network, a plurality of networks, a local computer, or the like. The actual algorithms for each operation, examinee identification, and/or any that may be required for a calibration program (to determine the physical pixel size of display monitor 227 to keep stimuli of the same pixel size the same physical size) being structured in a manner as would be understood by one of skill in the art.

Test stimuli 213 are represented by any of the small discrete elements that together constitute an image, such as pixels, and may be transmitted from a video controller (not shown) within computer 201 or through server(s) 233 to display monitor 227 having a viewable area representing the surface where the pixels are output. Computer 201 monitors the examinee's response, which is entered by, preferably, the use of a user input device 209. It also displays test stimuli 213.

Once the examinee's test scores or results are available, these may appear on a display device, such as a monitor 227 or through use of an output device, 205, such as a printer, via test result data storage 225. Connection 200b links 200a to a device that provides information and services, such as server(s) 233.

Figure 3A:
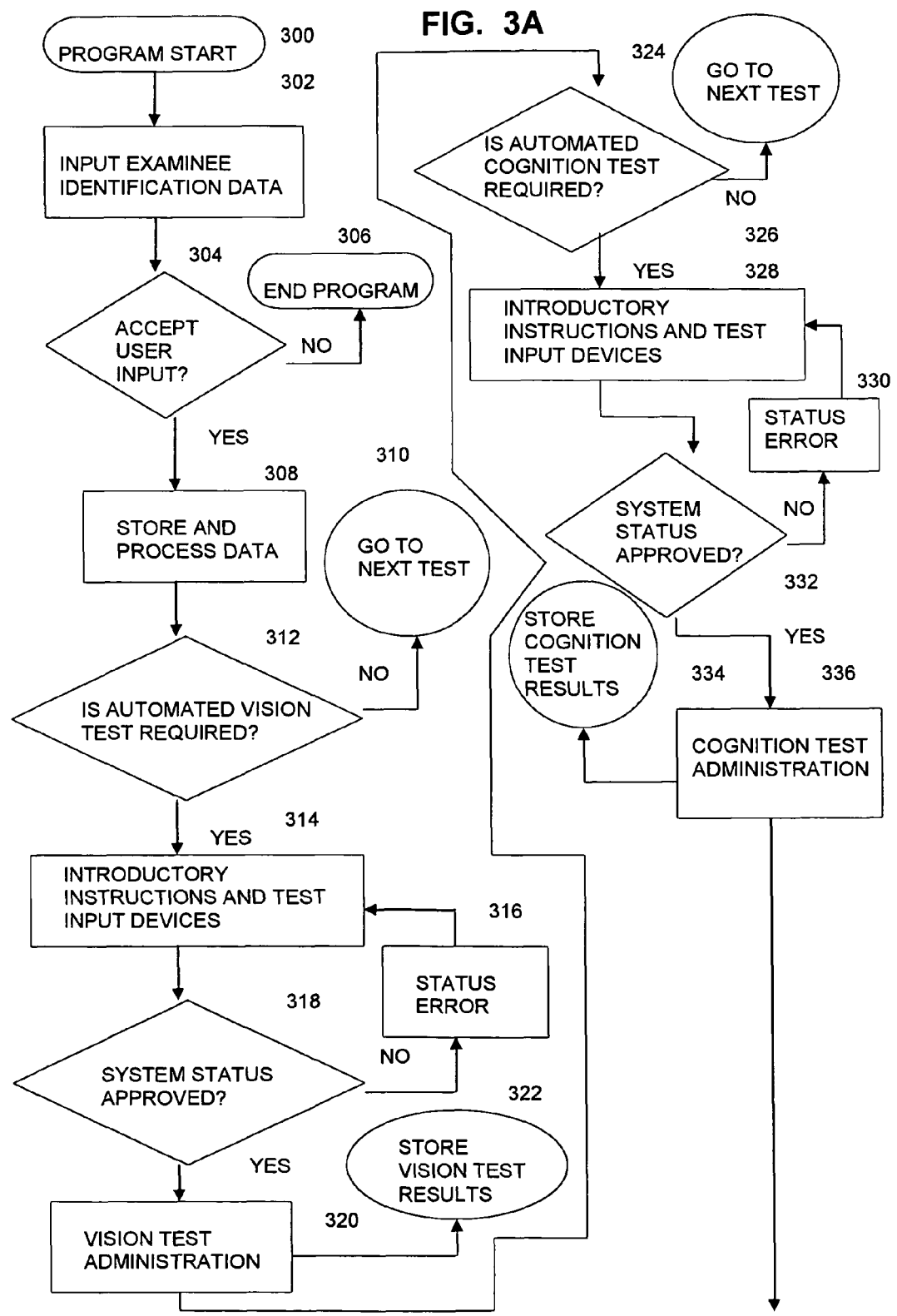

Referring to FIG. 3A, shown there is at least one embodiment of the automatic systems and methods, a flow chart of the general overall operation of the system. This depiction allows the examinee to take a series of tests, a vision test, a cognition test, and/or an operation skills test, with an option of doing it all sequentially. This may or may not be performed on the same day, depending on the test results as well as the preferences and schedules of the examinee. For example, since this is a unitary system comprised of at least one test, if an examinee successfully passes a vision test, the examinee may automatically proceed to a cognition test or an operation skills test. Hence the tests may be available in any desired sequence. For this illustration, however, a vision test precedes a cognition test, which precedes an operation skills test. In this operation, for example, the system 100 begins (Step 300) with the prompting of the examinee for the input of identification data (Steps 302-304). The program ends (Step 306) if the examinee's identification data is rejected. As long as the identification data is accepted, the examinee's data is stored and processed (Step 308). The examinee is prompted to declare whether or not an automated vision test is required and/or desired (Step 312). The examinee has the option to proceed to the next test (Step 310). When the examinee indicates that a vision test is required (Step 310), automated instructions on the vision test(s) are provided (Step 314) to the examinee through audio, video, text, images, or a combination thereof. Sample questions may or may not be provided. The system may determine if user input devices 109 are operational and if the examinee demonstrates an understanding of these devices based on input signals received when the examinee operates them. (The examinee is generally allowed the option to skip this section if desired because a system that is not functioning should be obvious to one skilled in the art.)

When the system status (Step 318) is rejected, due to improper use or condition of the input devices, a status error appears (Step 316). Step 314 is repeated. When the system status is approved, particularly through a successful sweep of the input devices and/or the examinee's use of these devices, a vision test administration (Step 320) initiates. Vision test results are stored (Step 322) in the test result data component 125. These may be available for review though output device 105.

In the next test sequence, the system proceeds with prompting the examinee to respond (Step 324) to whether or not an automated cognition test is required. The examinee has the option of proceeding to the next test (Step 326) if required and/or desired. Automated instructions on the cognition test(s) are provided (Step 328) to the examinee through audio, video, text, images, or a combination thereof. Sample questions may or may not be provided. The system may determine if user input devices 109 are operational and if the examinee demonstrates an understanding of these devices based on input signals received when the examinee operates them. (The examinee is generally allowed the option to skip this section if desired because a system that is not functioning should be obvious to one skilled in the art.)

When the system status (Step 332) is rejected, due to improper use or condition of the input devices, a status error appears (Step 330). Step 328 is repeated. When the system status is approved, particularly through a successful sweep of the input devices and/or the examinee's use of these devices, a cognition test administration (Step 336) initiates. Cognition test results are stored (Step 334) in the test result data component 125. These may be available for review though output device 105.

In the next test sequence, shown in FIG. 3B, the system proceeds with prompting the examinee to respond (Step 338) to whether or not an automated operation skills test is required. The examinee has the option to end the program (Step 340) if required and/or desired. Automated instructions on the operation skills test(s) are provided (Step 342) to the examinee through audio, video, text, images, or a combination thereof. Sample questions may or may not be provided. The system may determine if user input devices 109 are operational and if the examinee demonstrates an understanding of these devices based on input signals received when the examinee operates them. (The examinee is generally allowed the option to skip this section if desired because a system that is not functioning should be obvious to one skilled in the art.)

When the system status (Step 344) is rejected, due to improper use or condition of the input devices, a status error appears (Step 346). Step 342 is repeated. When the system status is approved, particularly through a successful sweep of the input devices and/or the examinee's use of these devices, operation skills test administration (Step 336) initiates. Operation skills test results are stored (Step 350) in the test result data component 125. These may be available for review though output device 105. The entire test sequence ends (Step 354) once the system administers the protocol of acknowledgement of test completion (Step 352) with the examinee.

Figure 4:
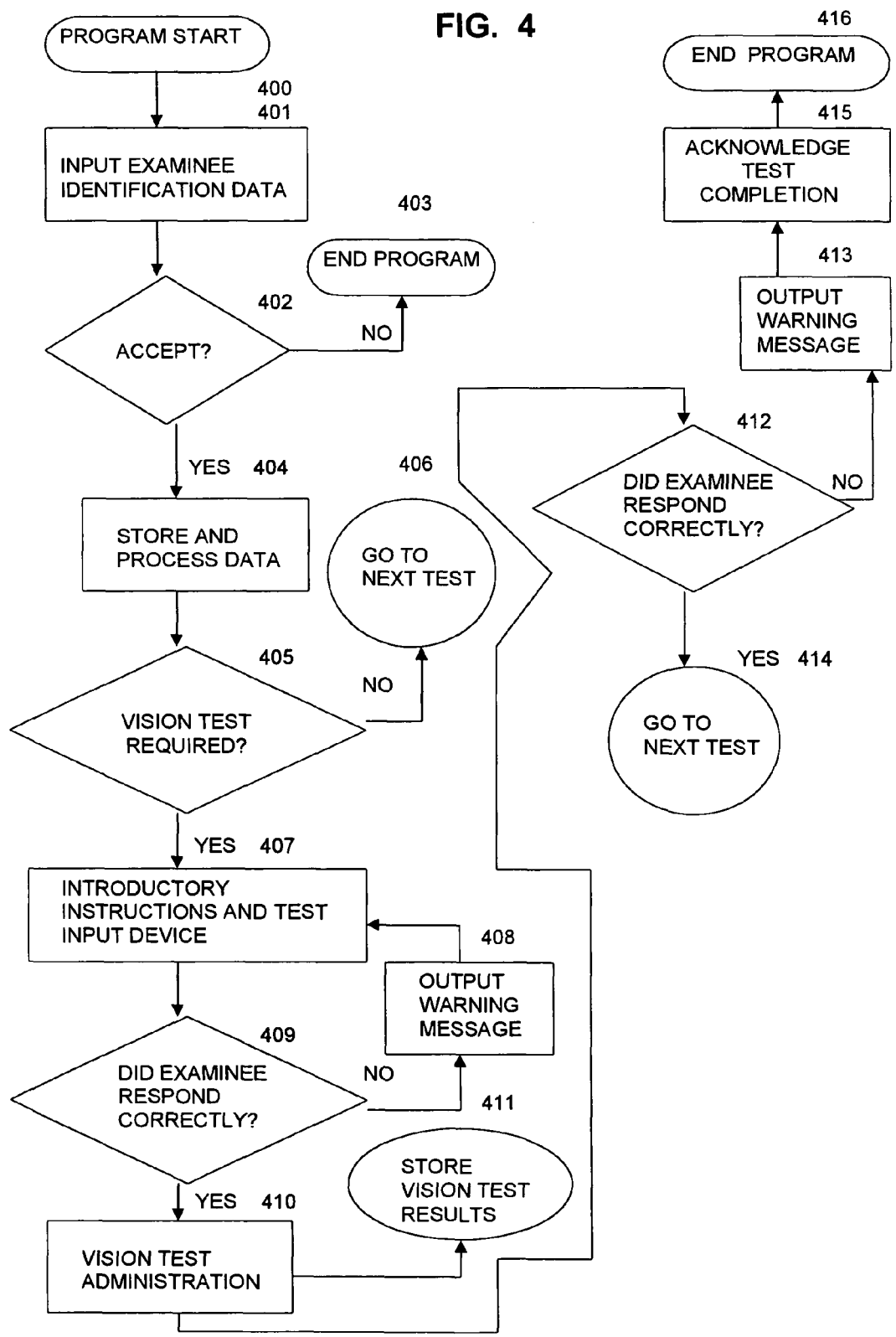
FIG. 4 shows an embodiment of a flowchart of an operation of steps for administering a vision test sequence.
Figure 5:
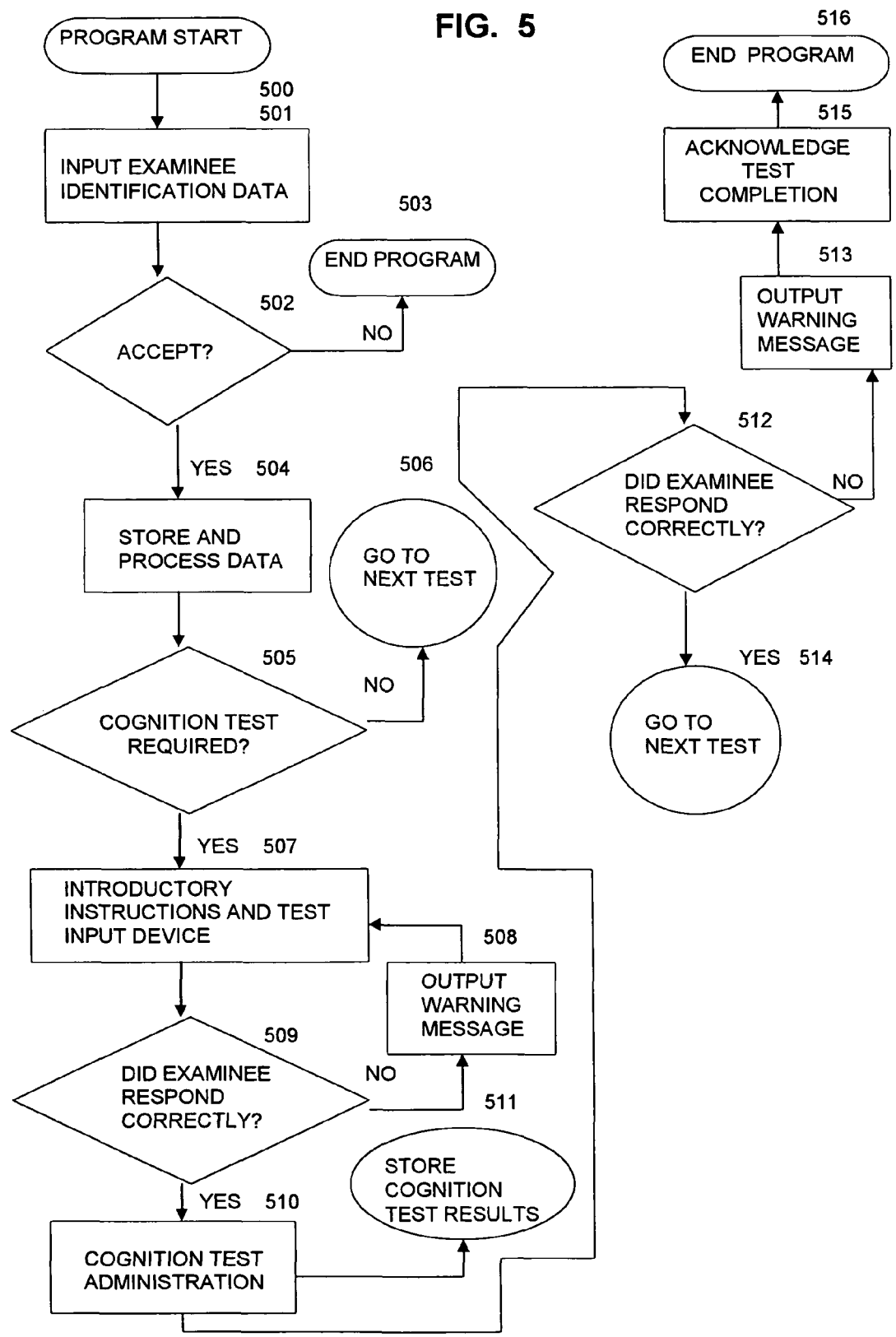
FIG. 5 shows an embodiment of a flowchart of an operation of steps for administering a cognition test sequence.
Figure 6:
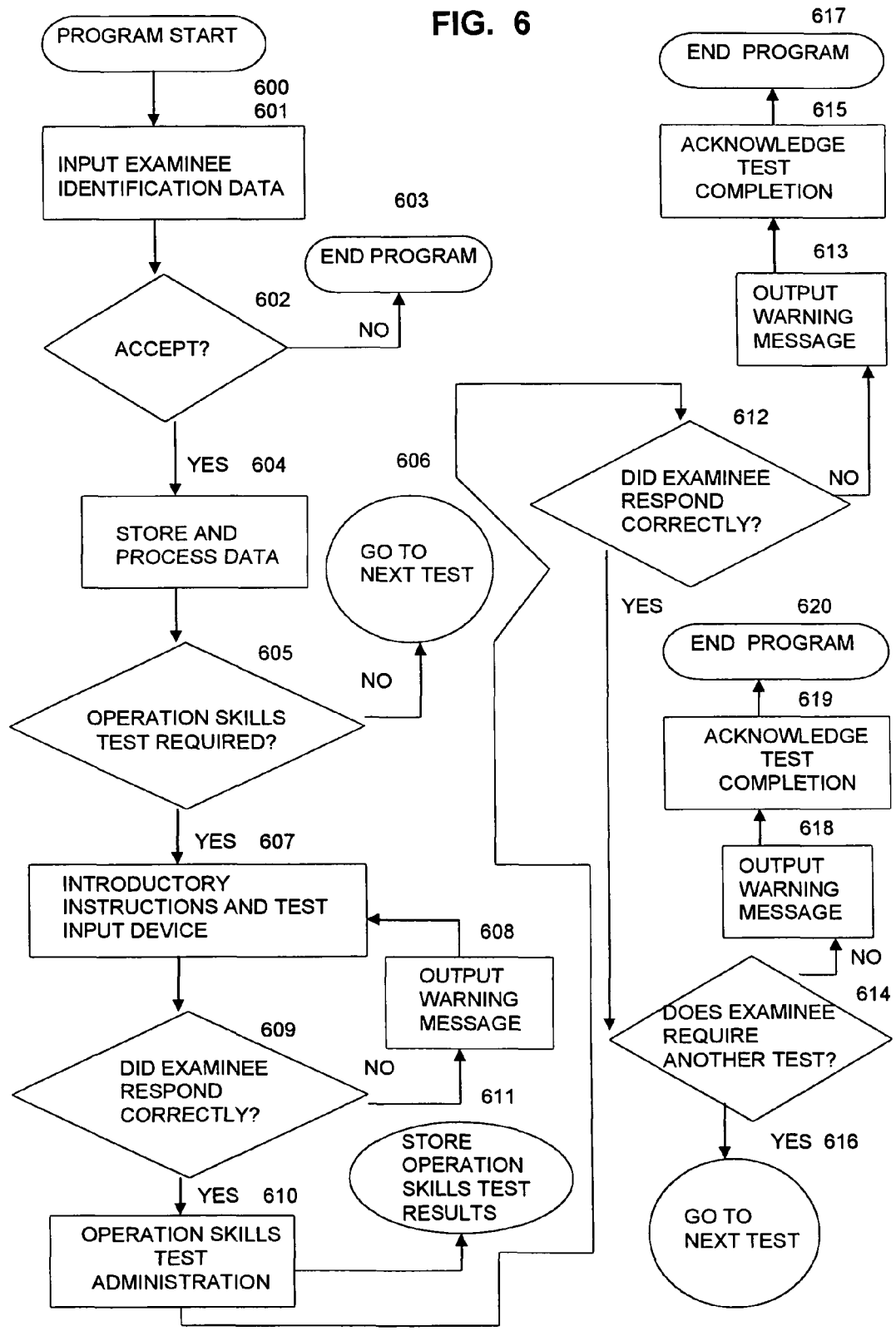
FIG. 6 shows an embodiment of a flowchart of an operation of steps for administering an operation skills test sequence.

In FIG. 4-6, flow charts are shown for various elements of the system 100.

FIG. 4 shows a flow chart for the specific operation of the steps for administering a vision test. In this operation, the system 100 begins (Step 400) with the prompting of the examinee for the input of identification data (Steps 401 402). The program ends (Step 403) if the examinee's identification data is rejected. As long as the identification data is accepted, the examinee's data is stored and processed (Step 404) and automated instructions on the vision test(s) are provided (Step 407) to the examinee Sample questions may or may not be provided.

The system proceeds with prompting the examinee to respond (Step 405) to whether or not the automated vision test is required. The examinee has the option of proceeding to the next test (Step 406) if vision test(s) are not required, or, if vision test(s) is required, introductory instructions may appear and the testing of the input device occurs (Step 407). Sample questions may or may not be provided. The system may determine if user input devices 109 are operational and if the examinee demonstrates an understanding of these devices based on input signals received when the examinee operates them. The system may then determine if the examinee responds correctly (Step 409). An examinee who does not respond correctly will receive an output warning (Step 408) and repeat Step 407. (The examinee is generally allowed the option to skip this section if desired because a system that is not functioning should be obvious to one skilled in the art.)

When the system status is approved, particularly through a successful sweep of the input devices and/or the examinee's use of these devices, vision test administration (Step 410) initiates. When the examinee responds correctly (Step 412), the examinee may proceed to the next test (Step 414). An output warning is issued to the examinee who does not respond correctly to the queries. Vision test results are stored (Step 411) in a test result data component 125. These may be available for review though output device 105. The test ends (Step 416) once the system administers the protocol of acknowledgement of test completion (Step 415) with the examinee.

FIG. 5 shows a flow chart for the specific operation of the steps for administering a cognition test. In this operation, the system 100 begins (Step 500) with the prompting of the examinee for the input of identification data (Steps 501-502). The program ends (Step 503) if the examinee's identification data is rejected. As long as the identification data is accepted, the examinee's data is stored and processed (Step 504) and automated instructions on a cognition test(s) are provided (Step 507) to the examinee. Sample questions may or may not be provided.

The system proceeds with prompting the examinee to respond (Step 505) to whether or not the automated cognition test is required. The examinee has the option of proceeding to the next test (Step 506) if cognition test (s) are not required or, if cognition tests are required, automated introductory instructions appear and the testing of the input device occurs (Step 507). Sample questions may or may not be provided. The system may determine if user input devices 509 are operational and if the examinee demonstrates an understanding of these devices based on input signals received when the examinee operates them. The system may then determine if the examinee responds correctly (Step 509). An examinee who does not respond correctly will receive an output warning (Step 508) and repeat Step 507. (The examinee is generally allowed the option to skip this section if desired because a system that is not functioning should be obvious to one skilled in the art.)

When the system status is approved, particularly through a successful sweep of the input devices and/or the examinee's use of these devices, cognition test administration (Step 510) initiates. When the examinee responds correctly (Step 512), the examinee may proceed to the next test (Step 514). An output warning is issued to the examinee who does not respond correctly to the queries. Cognition test results are stored (Step 511) in the test result data component 125. These may be available for review though output device 105. The test ends (Step 516) once the system administers the protocol of acknowledgement of test completion (Step 515) with the examinee.

FIG. 6 shows a flow chart for the specific operation of the steps for administering an operation skills test. In this process, the system 100 begins (Step 600) with the prompting of the examinee for the input of identification data (Steps 601-602). The program ends (Step 603) if the examinee's identification data is rejected. As long as the identification data is accepted, the examinee's data is stored and processed (Step 604) and automated instructions on operation skills test(s) are provided (Step 607) to the examinee. Sample questions may or may not be provided.

The system proceeds with prompting the examinee to respond (Step 605) to whether or not an automated operation skills test is required. The examinee has the option of proceeding to the next test (Step 606) if operation skills test(s) are not required or, if operation skills tests are required, automated introductory instructions appear and the testing of the input device occurs (Step 607). Sample questions may or may not be provided. The system may determine if user input devices 109 are operational and if the examinee demonstrates an understanding of these devices based on input signals received when the examinee operates them. The system may then determine if examinee responds correctly (Step 609). An examinee who does not respond correctly will receive an output warning (Step 608) and repeat Step 607. (The examinee is generally allowed the option to skip this section if desired because a system that is not functioning should be obvious to one skilled in the art.)

When the system status is approved, particularly through a successful sweep of the input devices and/or the examinee's use of these devices, the operation skills test administration (Step 610) initiates. An output warning (Step 613) is issued to the examinee who does not respond correctly to the queries. Operation skills test results are stored (Step 611) in a test result data component 125. These may be available for review though output device 105. The test ends (Step 617) once an output warning message is issued (Step 613) and the system administers the protocol of acknowledgement of test completion (Step 615) with the examinee. When the examinee responds correctly (Step 612), the examinee is prompted to take an optional next test (Step 614). The examinee may proceed to the next test (Step 616). When the examinee declines an optional next test, an output warning message is issued (Step 618). The test ends (Step 620) once the system administers the protocol of acknowledgement of test completion (Step 619) with the examinee.

Vision, defined as the act or power of seeing, may include tests of vision function, vision condition, vision status, or the like. Vision function defines the various functions of the structure of an eye. This may include but not be limited to color vision, contrast sensitivity, peripheral vision, visual acuity, and visual field. However, vision function may also screen individuals for cognitive deficits. As an example, vision function may aid in the screening of dementia and other neuropsychological and neuromotor disorders that are associated with visual difficulties yet cannot be detected through contemporary vision testing techniques. Known studies link dementia, including Alzheimer's Disease, with decreased visual acuity under low luminance Vision condition defines eye diseases, infectious causes, nutritional and metabolic factors, refractive error, and trauma. Vision status generally screens individuals for visual maladies. Vision status generally measures and evaluates the structure and/or components of an eye.

When vision testing is employed, personal condition relates to eye disease, eye condition, eye injury, and other possible disorders or ailments.

As used herein, the word "knowledge" and its variants are intended to be non-limiting, such that recitation of items in a list is not to the exclusion of other like items that may also be useful in the materials, compositions, devices, and methods of my improved automatic systems and methods. Therefore, an automatic cognition test(s) and/or the operation skills test(s) of various embodiments may incorporate the measurement and evaluation of knowledge in whole or in part.

Knowledge tests are a fundamental part of education, law enforcement, medicine, military, security, and transportation, among others.

In applications such as transportation license tests, knowledge tests are commonly referred to as written tests. A knowledge test generally comprises safety, laws, identification, and reasoning as these relate to specific vehicles in motion. Among automobile drivers, for example, the knowledge test usually gauges an individual's understanding of the "rules of the road", such as an understanding of accident prevention, pavement marking identification, safety rules, signal identification, traffic laws, traffic signage identification, and vehicle equipment. Such knowledge tests vary according to state and classifications of drivers' licenses.

In applications other than automobile transport, knowledge tests may comprise rules such as those governing agriculture, aviation, education, law enforcement, maritime, military, motorcycling, rail, safety, security, space, and trucking, among others.

Mental functions such as the ability to think, reason, and remember define cognition, which is sometimes referred to as mental status. Cognitive capabilities allow individuals to demonstrate their ability to at least think, reason, or remember. Since awareness, perception, and judgment, in addition to reasoning, define the mental process of knowing, then visual attention, defined by skills such as speed of target detection, divided attention, distraction, and peripheral awareness, may be classified as a cognition tool. Mental function is objectively assessed by mental status tests. These tests, referred to as cognition tests, screen individuals for cognitive impairment, improvement, or deterioration. Therefore, cognition tests may include at least one of visual attention, knowledge, mental abilities, or the like.

Cognitive aspects may also be selected from a group of at least one of perceptual skills, psychomotor skills, attention skills, memory skills, decision making/problem solving skills, or meta-cognitive skills depending on the needs of the client.

Personal conditions associated with cognition include but are not limited to such conditions as autism, dementia, Alzheimer's disease, Parkinson disease, hyperactivity, Attention Deficit Disorder, depression, Post Traumatic Stress Disorder (PTSD), Traumatic Brain Injury (TBI), learning disabilities, and other possible neuromotor, neuropsychological, and neurological conditions.

Still further, a knowledge test may be integrated into an operation skills test, a vision test may be combined with a cognition test, and any other methods within the improved automatic systems and methods may be combined thereof.

Operation skills form an essential component of comprehensive tests. Operation skills may include but not be limited to operating, navigating, controlling, driving, flying, moving, riding, gliding, steering, maneuvering, sailing, or the like. Although operation skills tests are primarily used in transportation license test applications, where applicants and licensees are required to prove competence in operating vehicles in motion, these tests may also be used to demonstrate the ability to operate or move predetermined items. At driver's license test bureaus, for example, the driving test, an operation skills test, allows examinees to actually drive a motor vehicle on or off the road in order to demonstrate the ability to safely operate a motor vehicle. Driving tests vary for different classifications of drivers' licenses.

Information data is defined as biometrics, thermal imaging, radio frequency identification (RFID tags), brain scans, or the like. Information data uniquely define each examinee according to predetermined measures and characteristics.

Driving skills, or skills required to operate any vehicle in motion, may be screened and monitored in the presently preferred embodiments. However, certain age-related declines that may be revealed include at least one of motor skills, reaction time, visual attention, route planning, sensory skills, or the like.

Data protection includes but is not limited to at least one of following: anomaly detection services, misuse detection services, data encryption, Kerberos protocol, secure shell, secure electronic transaction, secure socket layer (SSL), contents authentication, user identification, electronic signatures, hash functions, network intrusion detection device, data protection, biometric entry, synthetic backups, snapshots, firewall, proxy firewall devices, user authenticity identification, coding, cryptographical material, or the like.

Measurement and evaluation scores and diagnoses may be provided to institutions such as organizations, clinics, hospitals, senior citizen centers, educational institutes, militaries, law enforcement agencies, transportation bureaus, government agencies, or the like for at least one of review, research, or other purposes. Adequate security of such private and sensitive data may be insured by data protection methods, the details of such techniques being well known to those skilled in the art.

When data protection mechanisms are integrated, personal data, identification, test scores, and the like comprise the data to protect. It is necessary to ensure state-of-the-art privacy, security, backup, integrity, and protection of personal data associated with test scores and results.

Test fraud prevention may include but not be limited to randomization of test design features, such as screens, and/or use of false tests. The examinee would not know whether or not the screen is part of the actual test.

Operation

According to one aspect of the preferred embodiment, the apparatus of the system generally incorporates means for displaying vision, cognition, and related images to an examinee; means for generating such image data, such as a means for transportation for a vehicle in motion (such as a road, space, track, or water) for simulating operation of a vehicle in motion to be outputted on the display means; means for generating instruction data to be outputted at least on the display means; means for inputting, processing, and storing personal information data; means for using personal information data for establishing identification or authentication; means for inputting response data from the examinee in response to the generated image data on the display means; and means for controlling operation of the display means, the image data generating means, the instruction data generating means, and the inputting means.

The controlling means includes components for screening at least one of vision, cognition, operation skills, or the like. The screening components are operatively connected to the image data generating means, the instruction data generating means, and the inputting means such that image data and instruction data are generated and displayed in coordination with the screening test sequences conducted by the said screening components, respectively, and response data inputted through the inputting means.

Alternative Embodiments

Of course it will be recognized that a wide range of changes and modifications, apparent to those skilled in the art, can be made to the preferred embodiments described above.

The following describes some alternative embodiments:

The system, apparatus, and method for automatic tests are conducted over a computing device, network, thin client, or any interconnected means for data exchange and storage, such as Internet(s), Intranet(s), or extranet(s), independent of location. A component for identification and authentication purposes may be incorporated to authenticate, establish, update, or modify the identity of the examinee.

To conduct such examinations, stimuli of different shape, size, speed, frequency, location, color, contrast, and/or intensity are displayed on the user's display model. Use of such stimuli affords, for example, a convenient manner for conducting computerized mechanisms of screening.

The test results may be automatically outputted in raw form (i.e., pure data, numbers) or may be processed by the system before being outputted. As one of skill in the art would understand, test results may be processed, rated, correlated, iced, stored, shared, or any combination thereof.

Any device that accepts information in digital or similar form and manipulates it for a result based on a sequence of instructions, such as a computer, mainframe, minicomputer, workstation or personal computer, network computer, plurality of network computers, or the like could be used with the embodiments described above. In addition, any forms that execute automation, applications, or operating systems could benefit from the presently preferred embodiments.

Computerized device(s) can be powered through various mechanisms. One example would include a disposable or rechargeable battery unit. Another example of a power source would include a plug for connecting the device directly into a wall outlet.

Alternative embodiments may include the use of desktop(s), laptop(s), palmtop(s), or thin client computer(s), among other computing devices.

In some embodiments, the system may consist of a computer network with a file server connected to a plurality of terminals as opposed to stand-alone computers. Each terminal would include a display, the input/interface devices and a local CPU circuit that received, transmitted or processed data with the central file server in running the test sequences.

The tests may be combined. One of skill in the art would understand that the order and duration of the test sequences may be switched. Further, the operation of the system may include the use of one or more than the test sequences illustrated, wherein different combinations and orders of test sequences are implemented. Even more, each separate test sequence may even consist of a combination of individual tests, such as a vision function test, a vision status test, and a vision condition test. Each separate test sequence may also consist of varying numbers of individual tests. The order and number of test sequences and individual tests would depend on the requirements of the particular application, as would be understood by one of skill in the art. These and other changes and modifications are to be understood as included within the scope of the improved automatic systems and methods, as defined by the appended claims, unless they depart therefrom.

Another embodiment is directed to a method for establishing fixation during automatic measurement and evaluation of at least one of vision, cognition, operation skills, or the like, particularly useful when conducted over a data transmission and exchange system, for example, as embodied in the system of FIG. 1A. It should be clearly understood, that the presently preferred embodiments is also applicable for use with other systems and methods that automatically assess at least one of a subject's vision, cognition, operation skills, or related capabilities.

Another embodiment is directed to a method for presenting false-positive and false-negative test stimuli to the subject, to ensure reliability, the details of such techniques being well known to those skilled in the art.

One of skill in the art knows that the preferred embodiments described above include an option for automatic feedback and results since client requirements may dictate whether or not such data and/or information are issued to examinee(s). Therefore, autonomous testing methods, scoring, and immediate output (such as feedback) may be available to the examinee.

In another embodiment, all functions of the apparatus are in each case controlled by way of at least one of the pertaining form that executes automation, such as software, an online program, or other data control mechanism and can be varied with respect to the type of the construction possibilities and/or configuration mechanisms.

In still another alternative embodiment, the system may comprise software, as well as a combination of software and hardware. It additionally may comprise an interconnected system of one or more workstations, electronic computing devices, and or automatic means of transmitting data.

In another embodiment, the system may comprise adaptable computer programs accessible to the computers and or work stations via either CDs, DVDs, external drives, flash drives, internet, intranet, or any other method for transporting and/or exchanging information.

Another embodiment may also provide customized individual packages, as well as multiple workstations connected to a network or a website.

Another embodiment may also comprise a database that may store responses and/or historical data of each user. The database may be local, wireless, and/or remote, and may be accessible via a data transmission and exchange system, such as the Internet or may be fully or partially available at a user's facilities.

Still another embodiment adjusts to educating a user with respect to measured performance level or need for safety tool. The educating tasks may involve gaming elements to further enhance the motivation of the user. The tasks preferably may start with easy problems and gradually may increase in the level of challenge. The use of immediate feedback, as well as elements of competition when appropriate, may be included.

Still further, another embodiment provides at least one of brain fitness, eye fitness, brain training, eye training, and other visual and/or cognitive exercises to teach and/or improve vision and/or cognition, among others.

While the embodiments described above may be customized to the optimal challenge level for the user, based on past and current performance analysis with online dynamic diagnosis of errors and biases, there are a variety of ways to screen the same basic skills and produce the relevant scientific information.

In another embodiment, alternative forced-choice procedure measures, in which examinees must discriminate which of the test stimuli differs from the others, are integrated through the design permitting this discrimination and hence defines the level of screening. Such stimuli may include but not be limited to Snellen ratio, optotype size, optotype speed, optotype color, optotype dimensionality, optotype position, and optotype contrast. Measures may include but not be limited to static visual acuity, dynamic visual acuity, and the like.

In a further embodiment, computerized images may contain letters, numbers, characters, sceneries, and/or sounds and may be arranged in row(s), size(s), strings, movement, or any combination thereof and include at least one letter, character, or object in a different orientation, color, pattern, or any combination thereof than the others presented on the image and to be read and responded to by an examinee.

The embodiments described above may include high versus low contrast stimuli used to screen visual acuity at smaller and larger characters, according to predetermined measures, such as Snellen ratios, where the position of the dissimilar character varies randomly across repeated test trials on a display screen.

In another embodiment, multilingual capabilities and assistive technology features, specifically those designed to actively engage examinees with disabilities, may include but are not limited to such features as automatic instruction, audio, text, tests, feedback, or the like.

Still further, another embodiment may also consist of methods of automatically determining the presence and amount of substances, such as toxins, carcinogens, alcohol, inhalants, pharmaceuticals, or illegal narcotics. Such substances may impact at least one of vision, cognition, or operation skills of examinees.

The embodiments described above may also be used to provide primary and/or supplementary screening of those who operate vehicles in motion.

The embodiments described above may include a biometrics feature and/or components that promotes security and uniquely identifies examinees through mechanisms such as physical human characteristic (e.g., of the retina, iris, acoustic spectrum of the voice (i.e., voiceprint), facial recognition, fingerprint(s), handwriting, pattern of finger lengths, etc.).

In another embodiment, the image data generating means automatically incorporates transportation image data, such as a road, and test pattern image data. The test pattern image data is structured to screen at least one of vision, cognition, operation skills, or the like such as those required for a vehicle in motion.

In a further embodiment, a transportation license application is provided through methods for measuring and evaluating at least one of vision, cognition, operation skills, or related conditions and capabilities. These may incorporate the steps of providing a display through which transportation image data and instruction data are presented to an examinee, conducting a predetermined test sequence with the examinee, and providing input devices through which the subject may respond to the said test sequences. A predetermined test sequence includes at least one of conducting a vision test sequence with the examinee, conducting a cognition test sequence with the examinee, or conducting an operation skills test sequence with the examinee. The steps for conducting a test sequence each includes at least one of the steps of simulating the operation of a vehicle in motion to be presented on the display, generating instruction data for providing instructions for the examinee during the screening test sequences, or determining whether the inputted response data is correct or incorrect.

Another embodiment provides an automatic method for comprehensively screening at least one of vision, cognition, operation skills, or related capabilities of the masses.

In another embodiment, automatic systems and methods allow for automatic mass measurement and evaluation of at least one of vision, cognition, operation skills, or the like.

Another embodiment includes a processor that determines from the analyzed data the stimuli appropriate for at least one of the visual, cognitive, operation skills, or related level.

In still another embodiment, a representation generator, for vision, cognition, and related skills, operably coupled to a tester generates an overall representation using an examinee's responses. This representation may be used in a variety of diagnostic processes.

Another embodiment provides a computer software storage device that includes a program that executes the described method. The automatic method may be used for screening at least one of dementia, Alzheimer's disease, Parkinson disease, or other neuropsychological and neuromotor conditions.

There is yet additionally provided another embodiment that teaches an automatic method for diagnosing cognitive ability of an examinee, including the steps of screening a cognitive level of an examinee and comparing the screened cognitive level to data stored in a database, so as to at least one of measure, diagnose, monitor, or evaluate conditions such as dementia, Alzheimer's disease, Parkinson disease, and learning disabilities.

In another embodiment, instant feedback on strengths and weaknesses maneuvering adverse conditions are provided to an examinee. When operating a vehicle in motion, such as a motor vehicle, adverse conditions include but are not limited to at least one of the following: transportation site features (such as pavement), slippery pavement, various weather conditions (such as snow, rain, wind, dust, fog, smoke, haze) solar glare, night glare, ambient lighting conditions, traffic volumes, pedestrian movements, or vehicle mechanical problems (such as a blown tire). Vehicle mechanical problems may be involuntary (such as a failed engine or motor) or voluntary (such as control (such as a steering wheel, pedal, etc.) and/or misuse), among others.

The automation, integration, and/or simulation of such conditions and situations are obvious to those skilled in the art.

Still further is another embodiment that teaches an automatic method for at least one of educating, screening, or testing examinees and others on adverse conditions. The method(s) may include the steps of presenting stimuli relevant to adverse conditions, receiving motion input from the examinee in response to a stimulus, analyzing the aspects of at least one of cognitive, visual, operation skills, or related capabilities of the input, interpolating the analyzed aspects as these relate to vehicles in motion, adjusting a stimulus according to the analyzed aspect, and repeating the steps of presenting, receiving, analyzing, interpolating and adjusting one or more times.

In another embodiment, additional software and/or networking may be included with the device to allow for the automatic screening of at least one of vision, cognition, operation skills, related conditions, capabilities, or the like. For example, a test for school age children, may involve more game-like apparatuses and methods.

Another embodiment teaches cognition measurement and evaluation following a stroke, a head injury, or other type of trauma-related cognitive decline, as well as alcohol or drug related decline.

In another embodiment, a distributed system is created using a tester Web server operably coupled to a browser via the Internet. The tester Web server serves pages to the browser implementing this system.

In another embodiment, a measurement apparatus includes an electronic test pattern for display of test patterns to an examinee, an examinee response input device for recording an examinee's response to a test pattern, and a tester operably coupled to both for conducting the measurement.

Another embodiment includes a database for storing the analyzed data, where the data may relate to at least one of the norms, probabilities, or statistics of at least one of vision, cognition, operation skills, or the like. Analyzed data may be data regarding motor skills, complex/continuous motor skills, time required to move the stimulus, movement smoothness, complex eye hand coordination, hand-hand coordination, and/or eye-foot coordination.

Another embodiment includes a database for automatically storing and analyzing identification authentication data to readily identify an examinee. The system may also include a video and/or audio input and/or output device to automatically provide instructions in one or several different languages.

In another aspect of the presently preferred embodiment, a selected visual field test pattern is presented to a subject with an automatic means to prevent cheating and dishonorable test-taking practices, such as randomization of visual field test patterns. The user may select a missing or distorted visual field test pattern using an input device, when a random series of visual field test patterns, such as those of differing contrasts, are presented to the user. The user's responses are automatically recorded and evaluated. Automatic output is provided as at least one of feedback, results, scores, reviews, classifications, rejections, simplified output, pass/fail determinations, graphical/statistical reprentations, or comparative analyses.

In another embodiment, vision, cognition, and related representations are automatically correlated with known causes of vision and/or cognition defects. These are stored in a diagnostic database operably coupled to a diagnostic tool configured to perform multiple functions, such as a server, accessible via a connectivity device that facilitates data transmission, such as the Internet, a local network, or some wireless network A representation is automatically sent to the diagnostic tool which uses an AI artificial intelligence engine to establish a diagnosis.

Another embodiment teaches an automatic method for diagnosing at least one of cognitive, visual, or related ability of a user, including the steps of testing at least one of cognitive, visual, or related level of a user and comparing at least one of cognitive, visual, or related level to, for example, data stored in a database, so as to diagnose at least one of brain diseases, brain injuries, brain disorders, eye diseases, eye injuries, eye disorders, or various neuromotor disorders. These include but are not limited to age-related macular degeneration, autism, Alzheimer's disease, dementia, diabetic retinopathy, glaucoma, Parkinson disease, and learning disabilities, among others.

In another embodiment, test presentations may be automatically adjusted to eliminate inattention or reduce the incidence of aftereffects that can develop, especially when, for example, simulators, such as driving simulators, are incorporated in the evaluation process.

Another embodiment provides the icing of storage and the collation of data through at least one of a locally, remotely, wirelessly, or virtually centralized database. This allows the automatic tracking of vision, cognition, operation skills, and related measurement and evaluation programs.

In still another alternative embodiment, customized reporting may be provided for studies, such as epidemiological studies, and can be tailored to virtually any specific request.

In an alternative embodiment, a vehicle in motion is reliably simulated so that an examinee feels as if he or she is actually operating a vehicle in motion.

In yet another embodiment, at least one of a driving simulator, display device, or the like is used so that an examinee does not tire easily, is swiftly and adequately screened, has easy access to all of the controls, and experiences little or no adverse reactions such as cybersickness, driving simulator sickness, or the like.

An alternative embodiment automatically simulates a vehicle in motion.

In another embodiment, a mechanism that simulates an environment of a vehicle in motion may also produce immediate sensory, visual, or audio response to an examinee's manipulation of such an apparatus.

In still another alternative embodiment, at least one of a display device, a simulator (such as a driving simulator), or the like may be optionally used as an educational tool to demonstrate how to respond to adverse conditions.

In one possible embodiment, a low-cost driving simulator or other device that simulates environments and situations to train, test, and/or educate examinees may be used to measure and evaluate at least one of vision, cognition, operation skills, or the like. Such simulation may offer the benefit of self-customization, among other features, to reduce the likelihood of simulator sickness, which results from a disparity between the actual visual image position verses the expected position in a dynamic situation. Hence the testing should be done as effectively and as swiftly as possible, without compromising thoroughness. This will reduce the incidences of simulator sickness and aftereffects.

Some embodiments may also allow for the objective and rapid evaluation of individuals with strokes, cognitive maladies, and other neurological disorders, such as Parkinson's disease, a progressive, neurodegenerative disease characterized by tremor and impaired muscular coordination. Traditional testing methods of dementia patients tend to be time-consuming and challenging.

In a further embodiment, there are automatic assessments such as strength, general mobility, head flexibility, neck flexibility, working memory, visualization of missing data, visual attention, field of view, and/or visual search, etc. among others, of examinees.

In another embodiment, a simulator is used to screen at least one of vision, cognition, operation skills, responses to ambient lighting, or adverse conditions for educational purposes, clinical reviews, medical evaluations, military reviews, licensure to operate a vehicle in motion, or any combination thereof.

In an alternative embodiment, at least one of an examinee's visual capabilities, cognitive capabilities, operation skills, or the like are measured and evaluated by automatically exposing the examinee to certain conditions, such as ambient light conditions.

In another embodiment, conditions such as glaucoma, diabetic retinopathy, cataracts, and Age-related Macular Degeneration, low vision, autism, stroke, head injury, dementia, depression, Alzheimer's disease, Parkinson disease, Post Traumatic Stress Disorder, and other possible neuromotor, neuropsychological, neurological, and medical conditions, among others, may be automatically detected and monitored. Some conditions, such as Traumatic Brain Injury, may not be evident until days, weeks, months, or even years after an impact event. Therefore, automatic testing offers many benefits over traditional evaluations.

In an alternative embodiment, an examinee's knowledge is assessed through responses to a display of select matter as it relates to a specific mode of transport, such as street signs, traffic control devices, pavement markings, signal devices, railroad signs, air flight control signs, space travel signs, and maritime signs, among others.

In a further embodiment, high versus low contrast stimuli are used to screen visual acuity at smaller and larger characters, according to predetermined measures, such as Snellen ratios, where the position of the dissimilar character varies randomly across repeated test trials on a display screen.

In another embodiment, authentication identification data of examinees and test fraud prevention mechanisms improve safety and security.

Advantages

In view of the disadvantages and shortcomings present in the prior art, improved automatic systems and methods provide valuable measurements and evaluations of at least one of the vision, cognition, operation skills, or the like.

The preferred embodiments described above provide important advantages. In clinical testing, these embodiments provide particularly effective testing of a subject, allowing objective and economical measures. In transportation applications, these embodiments offer rapid testing and monitoring of the masses who obtain or maintain a license to operate a vehicle in motion. In military settings, these embodiments afford uniform screening tools for recruits, soldiers, and veterans. In security, education, and health, these embodiments offer standardization and equality. Importantly, automatic systems and methods promote safety on and off the transportation infrastructure.

The advantages achieved by the embodiments described above are that a small and handy measuring apparatus was created in contrast to the known large systems. The combination of the possible measuring operations permits the concentration of the functions of several systems on a single apparatus, which measures the important vision, cognition, operation skills, and related functions. Such evaluations and measurements are cost-effective and eco-friendly because they provide rapid, objective, and, importantly, automatic testing for the purposes and benefits of at least one of medicine, law enforcement, military, safety, security, or transportation, among others. As a result of the construction with low-cost elements and the utilization of existing elements (computer), it is possible to integrate the system into already existing systems. This results in a significant reduction of costs and a savings of space, energy, and potential e-waste, especially when unitary housing is integrated for all tests. Because the apparatus can be used without any problems in normal daylight, the operation becomes uncomplicated and convenient. Summarizing, there is the possibility for widespread use of the apparatus, for example, also among hospitals, security agencies, militaries, schools, and transport license bureaus, among others. As screening tests, these low-cost apparatuses may contribute to the detection, diagnosis, and, ultimately, treatment of dangerous conditions, diseases, disorders, and/or injuries. Within this scope, algorithms of any forms that execute automation already provide information with respect to measured values.

Still another major advantage of the presently preferred embodiment over the prior art is that the automatic technique may be employed for the masses of individuals who might not be easily tested using the prior art methods that employ non-automated devices. The present invention would also be beneficial in applications where trained ophthalmologists, physicians, and other clinicians are not available, such as driver's license test bureaus, rural areas, outer space (such as NASA or any agency or entity associated with space travel) applications, maritime environments, flight settings, security facilities, or military applications.

The presently preferred embodiment offers exceptional advantages when measuring and evaluating examinees at or away from transportation license agencies, such as a driver's license test bureaus, particularly if the identification authentication component is utilized for identification purposes of the examinee.

Other examples of the utility of the presently preferred embodiment include the automatic screening of individuals suffering from at least one of brain injury, brain trauma, brain disease, cognitive deficit, eye disease, eye injury, eye trauma, neuropsychological disorders, or movement disorders (such as neuromotor disorders). Such individuals may often not be aware that that they have such a condition, malady, or disorder through the use, if any, of other traditional testing devices and/or methods.

Still further, from the description above, a number of additional advantages of some embodiments of my automatic systems and methods become evident:

(a) Automatic systems rapidly, objectively, uniformly, and effectively screen at least one of vision, cognition, operation skills, related capabilities or conditions of individuals for medical purposes.

(b) Automatic systems actively engage at least one of speakers of other languages, individuals with disabilities, or individuals with special needs.

(c) Automatic systems effectively measure and evaluate at least one of vision, cognition, operation skills, or related capabilities of individuals for security purposes.

(d) Automatic systems effectively screen at least one of vision, cognition, or related capabilities of individuals in a simple, rapid, and economical manner.

(e) Automatic systems effectively screen at least one of vision, cognition, or related capabilities of individuals for the purpose of at least one of education, military, safety, security, or transportation.

(f) Automatic methods of testing and evaluating the visual field of the masses, such as a three-dimensional Amsler grid visual field test, made entirely or in part by simplified output, an input device (such as described earlier), autonomous testing processes, testing stimuli that can be rapidly performed at a selected duration of time, means to prevent cheating and test fraud, means for identification authentication purposes, and the means for testing examinees and displaying, moving, and transmitting data such as over a computing device, network, or interconnected means for data exchange and storage, independent of location, to screen users for medical purposes, security objectives, or any license to operate a vehicle in motion.

(g) Automatic systems measurably analyze and evaluate at least one of vision, cognition, operation skills, or the like of an individual using an interface with the test examinee that provides a familiar environment for him or her.

(h) Automatic systems and methods measurably analyze, gauge, and evaluate at least one of vision, cognition, operation skills, or the like particularly necessary to operate a vehicle in motion, and the like.

(i) Automatic systems and methods may further include determining from the cognitive aspects a cognitive level of the examinee.

(j) Automatic testing of the masses afford benefits of objective, rapid, and uniform measures of at least one of vision, cognition, operation skills, or the like under certain circumstances. However, other embodiments may also be preferred, under the same or other circumstances. Furthermore, the recitation of one or more preferred embodiments does not imply that other embodiments are not useful, and is not intended to exclude other embodiments from the scope of the presently preferred embodiments.

(k) Automatic systems and methods may be employed for the masses of individuals who seek to improve at least one of visual, cognitive, operation skills, or the like through exercise and training programs. Such programs may include but not be limited to at least one of brain fitness, eye fitness, brain training, and eye training.

(l) Automatic systems and methods allow for measurements and evaluations of at least one of cognition, operation skills, vision, or the like of the masses of individuals for at least one of medical evaluation, security review, or licensure to operate a vehicle in motion not readily testable using the prior art technology.

(m) Automatic systems and methods provide for the ability to combine and deliver a number of testing methodologies such as measuring and evaluating high contrast visual acuity, low contrast visual acuity, static visual acuity, dynamic visual acuity, visual attention, knowledge, cognition, operation skills, and the like.

(n) Automatic systems and methods of measurement and evaluation of at least one of vision, cognition, operation skills, or the like afford test administration autonomously or by anyone, even with the most rudimentary of computer skills.

(o) Automatic systems and methods provide an apparatus for measurements that are easy and economical to produce comprised of conventional currently available materials that lend themselves to standard mass production manufacturing techniques. Such embodiments may be eco-friendly and significantly reduce the environmental impacts associated with paper, plastics, and electronic wastes ("e-wastes").

(p) Automatic systems and methods do not require formalized training due to at least one of automatic instruction, administration, or scoring mechanisms.

(q) Automatic systems and methods provide uniform and objective measures of at least one of vision, cognition, operation skills, or the like independent of when and where such measures are performed and that may allow at least one of local, regional, national, global testing, or collection of data to permit analysis and evaluation.

(r) Automatic systems and methods provide at least one of measurement and evaluation of at least one of vision, cognition, operation skills test, or the like that may be standardized within each application. For example, in transportation license applications, such as those required to obtain or maintain a driver's license, certain "rules of the road" and driving skills are necessary. These are different than the knowledge and operation skills required to operate other vehicles in motion, such as a train, a truck, a ship, a military tank, an airplane, a tractor, a motorcycle, or a spacecraft. Standardized cognition and operation skills tests should be available for each of these areas of transportation. Among drivers of automobiles, for example, a nationally standardized driver's license test may reduce collisions among interstate drivers because drivers in one state would be tested on features of all states.

(s) Automatic systems and methods create useful measurements and evaluations of an examinee by permitting the examinee to respond to at least one of imagery, sounds, motion pictures, or stimuli on a display device, such as an electronic screen.

(t) Automatic systems and methods provide an automatic apparatus that is simple and inexpensive to manufacture and durable in use.

(u) Automatic systems and methods provide an automatic apparatus that is safe for an examinee to use.

(v) Automatic systems and methods quickly and accurately ascertain at least one of vision, cognition, operation skills, or related capabilities of an examinee.

CONCLUSION, RAMIFICATION, AND SCOPE

Accordingly, the reader will see that the automatic systems and methods of the various embodiments provide a more reliable, faster, yet economical device that can be used by persons of almost any age.

Furthermore, the automatic systems and methods have the additional advantages in that:

rapid, objective, uniform, economical, and effective measurements and evaluations are provided of at least one of vision, cognition, operation skills, or the like;

implementation ultimately yields improvements to national and international safety and security;

implementation ultimately improves safety in at least one of roads, rails, skies, waters, or space for transportation applications;

implementation ultimately conserves energy, prevents deforestation, and reduces pollution associated with paper, computers, software, and e-wastes;

implementation can ultimately engage at least one of speakers of other languages, individuals with disabilities, or individuals with special needs;

implementation ultimately ensures equality and uniformity of testing in education, military, safety, security, and transportation sectors;

implementation ultimately improves safety and security through authentication identification data of examinees and test fraud prevention mechanisms; and implementation ultimately permits rapid, objective, and effective measurements for those who are transportation licensees or applicants, operate vehicles in motion, or seek licensure in the security, safety, health, military, and education fields.

In addition, novel mass systems and methods utilizing automation and identification technologies are proposed to measure and evaluate at least one of vision, cognition, operation skills, or the like. While the devices, methods, and systems disclosed hereinabove and illustrated in the drawings have been adapted for detecting and assessing the presence of at least one of an eye disease, eye trauma, eye injury, brain injury, brain disease, brain trauma, physical disability, glaucoma, age-related macular degeneration (AMD), diabetic retinopathy, stroke, dementia, Alzheimer's disease, Parkinson disease, hyperactivity, Attention Deficit Disorder, learning disabilities, low vision, autism, depression, Post Traumatic Stress Disorder, neuromotor, neuropsychological, or neurological conditions, the devices, methods, and systems disclosed may also be used or adapted for detecting or assessing other types of vision abnormalities, cognitive abnormalities, or the like.

While the above description contains many specificities, these should not be construed as limitations on the scope of any embodiment, but as exemplifications of the presently preferred embodiments thereof. Many other ramifications and variations are possible within the teachings of the various embodiments. For example, the automatic systems and methods can incorporate measurements and evaluations of strength, general mobility, head flexibility, neck flexibility, working memory, visualization of missing data, visual attention, field of view, and/or visual search, etc. among others, of examinees; the automatic systems and methods can include measures such brain fitness, eye fitness, brain training, eye training, and other visual and/or cognitive exercises to teach and/or improve vision and/or cognition, among others.

Thus the scope of the embodiments should be determined by the appended claims and their legal equivalents, rather than by the examples given.

What is claimed as new and desired to be protected by Letters Patent is set forth in the appended claims:

1. An automatic system for testing, evaluating, screening, training, or any combination thereof for at least one of vision, cognition, or operation skills of an examinee comprising:

a computer for processing data wherein a computing environment is conducted over a network, thin client, or interconnected means for data exchange and storage;

an input device for recording response information from an examinee in response to test stimuli;

a linking device for linking data to at least one institution whereby said data can be automatically stored, shared, reviewed, and/or studied;

a display device configured for presenting test stimuli to an examinee and for displaying the test data received by the input device;

wherein said computer means includes:

a means for preventing test fraud;

a means for identifying the examinee;

a user identification input device, and a processing device for receiving said data from said input device to at least test, evaluate, screen, train, or any combination thereof a personal condition of said examinee.

2. An automatic system as claimed in claim 1, wherein the means for identifying the examinee includes at least one of voiceprint recognition, facial recognition, fingerprint recognition, handwriting recognition, pattern of finger lengths recognition, retina recognition, or iris recognition.

3. An automatic system as claimed in claim 1, wherein the input device is selected from at least one of a computer mouse, wireless mouse and pad, keyboard, touch screen, joystick, brake pedal, accelerator pedal, pedal, steering wheel, microphone, camera, horn, virtual reality device, or any combination thereof.

4. An automatic system as claimed in claim 1, wherein the user identification input device includes information data input by the examinee, biometrics, thermal imaging, radio frequency (RFID tags), or any combination thereof.

5. An automatic system as claimed in claim 1, wherein the display device is selected from at least one of a printer, or a monitor.

6. An automatic system as claimed in claim 1, wherein the computer means is selected from at least one of a desktop, a laptop, a palmtop, a thin client computer, a mainframe, a minicomputer, a workstation or personal computer, a network computer, a telecommunication device, or plurality of computers.

7. An automatic system as claimed in claim 1, wherein the personal condition includes at least one of an eye disease, eye trauma, eye injury, brain injury, brain disease, brain trauma, physical disability, glaucoma, age-related macular degeneration (AMD), diabetic retinopathy, stroke, dementia, Alzheimer's disease, Parkinson disease, hyperactivity, Attention Deficit Disorder, learning disabilities, neuromotor, neuropsychological, or neurological conditions.

8. An automatic system as claimed in claim 1, wherein the institution is selected from at least one of hospitals, senior citizen centers, schools, colleges, militaries, law enforcement agencies, transportation bureaus, clinics, government agencies, or any combination thereof.

9. An automatic system as claimed in claim 1, wherein the test stimuli differ in color, contrast, frequency, location, shape, size, speed, and/or intensity.

10. An automatic system as claimed in claim 1, wherein the means for preventing test fraud includes at least one of biometrics, data protection, randomization of screens, or false tests.

* * * * *